(12) United States Patent
Fish et al.

(10) Patent No.: US 8,401,875 B2
(45) Date of Patent: Mar. 19, 2013

(54) SECURED PERSONAL DATA HANDLING AND MANAGEMENT SYSTEM

(75) Inventors: Gila Fish, Mevasseret Zion (IL); Avner Korman, Herzlia (IL)

(73) Assignee: OS - New Horizons Personal Computing Solutions Ltd., Mevasseret Zion (IL)

( * ) Notice: Subject to any disclaimer, the term of this patent is extended or adjusted under 35 U.S.C. 154(b) by 109 days.

(21) Appl. No.: 12/849,971

(22) Filed: Aug. 4, 2010

(65) Prior Publication Data

US 2011/0224509 A1 Sep. 15, 2011

Related U.S. Application Data

(60) Provisional application No. 61/313,145, filed on Mar. 12, 2010.

(51) Int. Cl.
G06Q 10/00 (2012.01)
G08F 17/30 (2006.01)
(52) U.S. Cl. .............................. 705/3; 707/9
(58) Field of Classification Search .................. 705/1–3
See application file for complete search history.

(56) References Cited

U.S. PATENT DOCUMENTS

| | | | | |
|---|---|---|---|---|
| 6,539,380 | B1 * | 3/2003 | Moran | 707/783 |
| 6,830,549 | B2 * | 12/2004 | Bui et al. | 600/549 |
| 7,448,996 | B2 * | 11/2008 | Khanuja et al. | 600/300 |
| 2009/0062887 | A1 * | 3/2009 | Mass et al. | 607/60 |

* cited by examiner

Primary Examiner — Hiep V Nguyen
(74) Attorney, Agent, or Firm — Henry M. Sinai; IP-Partnership

(57) ABSTRACT

A system, method and personal apparatus for managing highly secured personal data is provided. The system and the personal apparatus are complementary, both providing highly secured personal data, mass, safe and secured data access, storage and management solutions, while serving the needs for managing and exchanging secured personal data with external services and data providers and with other such highly secured personal data users. The apparatus may be used independently of the system by securely connecting the apparatus to service providers. The apparatus, which is uniquely identified with a unique user, includes a sensor module comprising a plurality of biometric sensors for reading a plurality of personal biological identification parameters of the user and an authentication unit for positive authentication of the user's personal biological identification parameters stored in the authentication unit. The system is designed to securely serve the needs of conducting and maintaining multiple users' personal data access, storage, updating and retrieval capabilities. The method supports the safe and secured operation of the apparatus by its owner, in order to get access to the system and to exchange highly secured personal data with external pre-registered service providers and with other registered system users.

38 Claims, 9 Drawing Sheets

SECURED PERSONAL DATA HANDLING AND MANAGEMENT SYSTEM

CROSS REFERENCE TO RELATED APPLICATIONS

This application claims the benefit of U.S. provisional patent application No. 61/313,145 filed on Mar. 12, 2010 and incorporated by reference as if set forth herein

FIELD AND BACKGROUND OF THE INVENTION

The present invention relates in general to the need of modern computer age users to have easy, affordable, and immediate access to their personal information regarding many aspects of their daily life, including but not exclusively related to their financial, economical, work related sensitive data files, their medical updated records, other and important personal files and their many registered and favorite websites access data needs. The invention also relates to secured personal data exchange, storage and handling processes done through a combined computer, Internet and telephony based system.

More particularly, the invention relates to combined computers, Internet and telephony dedicated systems supporting for a plurality of users solutions to get access, store and manage their personal data in a safe and secured way, by using a personal data authenticator functioning as a smart and advanced token, to get a safe and highly secured access to the system and to store updated vast amount of their personal data on easy to carry tokens.

The ways, communication channels and the required data storage size and data throughput capacity of modern computer systems and their user's communication needs are fast expanding in the required operational performance needs, data storage capacity and associated required technical capabilities. Modern computer systems need in many cases also to support the communication needs between the users and various computer supported services, enabling the handling and exchange of very large files of data between services and information providers and clients. Such large files sizes handling systems are in many cases required to securely manage their users and clients textual, numeric, imagery, audio, graphics and many other personal data files of a highly sensitive information related to the system's users, or clients personal data. Such systems are typical to the needs of organizations such as hospitals, government and municipal agencies, banks, insurance companies and other financial institutes, which needs are rapidly changing towards higher data throughput and storage capacity, yet keeping the users and clients personal information in full security and confidentiality.

In parallel, today more and more users have the will to use new technological solutions and methods to be able to store and easily get access to their own personal data while storing it in small portable devices and through these devices also to be able to download, retrieve and manage most if not all their personal data and daily operational needs. The users may also have the need to use their personal ID data to create personal files and other private files and to have an access to other large size data files, through special highly secured dedicated computerized systems. By using such dedicated secured combined systems, the users will be able to securely transfer and exchange sensitive and private personal data and information with other authorized specific users and with suppliers of large scale size personal data files. These files may serve the growing secured personal data exchange, sharing and transfer needs of external services providers and suppliers using and generating highly personal data files, such as hospitals, banks, Insurance companies, government office and agencies, etc.

In order to get access to secured data files in most computerized systems users are usually required to be first recognized and identified by the computerized system as legitimate registered users, prior to getting access to the secured data files. Each one of these systems users is therefore required to first provide the computerized system with some data strings of secret information, unique to this user, in order to be recognized by the computerized system as a legitimate user and then the user is permitted to get entry access to the system. The process of the user being recognized and approved by a computerized system is called authentication. A two-factor authentication is an improved security process in which a user provides two types or means of his personal identification, one of which is typically a physical token, such as a card, and the other of which is typically something memorized, such as a security code. In this context, the two factors involved are sometimes spoken of or referred to as something a user has and something a user knows—a pass code. A common example of two-factor authentication is a bank card: the card itself is the physical item and the personal identification number (PIN) is the known data, as a second factor, that goes with the bank card.

Markets available hardware token generators may presently be used for authentication to enterprise systems. However, a hardware token generator only generates a token to be used by a user or a holder of the hardware token generator to manually supply the token for authentication. For example, a two factor authentication can require that the second factor be a "physical token," i.e., something the user has, that can produce (i.e., display) the second factor token (such as a numeric string) that the holder of the "physical token" can enter at a terminal providing access to a sought service. However, a drawback of a hardware token generator is that a lost or stolen hardware token generator can be used to breach security or for fraud. Another drawback is requiring a user to manage an additional physical token for authentication purposes. Another drawback is multiple hardware token generators are needed for multiple authentications to different systems. Also, a hardware token generator does not adequately prevent from phishing by hackers and criminals, because a two-factor authentication using presently available hardware token generator as the second factor, are still susceptible to "man in the middle" type attacks.

The prior art covering some of these capabilities is described in several publications as detailed herein.

A method for writing medical prescriptions, storing, and accessing patient medical records with improved portability and improved patient data security using a USB dongle device, is described in US Patent Application No. 20090204433, filed Aug. 13, 2009. The portable USB dongle device containing the patient records and software is easily removed and transported to other local terminals. The relevant patent describes a method for controlling access to medical records comprising: A) Providing a portable memory device which is able to store controlling software and said medical records; B) Providing a display device which is operationally connected to a microprocessor which will display said medical records & will selectively control a display of said medical records; and C) Using Fingerprint biometric authentication.

Medicard by Walletex Microelectronics Ltd. (http://www.walletex.com), from 6300 N.W. 97 Ave. Miami, Fla. 33178, USA, is a credit card size and shape USB flash memory for the user's medical records. MediCard has a large, double sided area that can be printed with the user's name, picture, doctors' names and phone numbers, information on allergies and medications, and other life-saving facts for emergency first-responders. It has enhanced security offering_Strong AES Encryption, Password protection, Memory partitioning (Read only part, Secured part, Public part), Large memory capacity (up to 8 GB), may contain both data and application software. Optional features are Biometric recognition, Magnetic strip.

US patent application No. 2008/0041940 A1; filed Jun. 4, 2007 partially covers some of the elements that were integrated into the Walletex Medicard device product. This patent application only includes two claims on a system which partially relates to the Medicard product as prior art. The first system claim is; A system of capturing and storing personal data, patient medical records and medical insurance and payment information comprising: a) providing a credit card-sized USB flash drive or similar device to store said patient medical records combined with a Smart Card or similar device to store said payment information including medical insurance and payment information such that said USB flash drive and Smart Card combination easily fits into one's wallet or worn on a necklace; and b) providing a USB jack and a means for emergency medical workers, hospital workers, and other health and medical workers to view and change said patient medical records; and c) providing a Smart Card and a means for health and medical workers to process said medical insurance and payment information, whereby said system will allow an individual to contain said patient medical record and said medical insurance and payment information in one small credit card-sized unit. Their second claim is: The credit card-sized USB flash drive or other device of claim 1 providing a mechanism for encrypting patient data such that it may only be viewed when a pass phrase, pin number, or similar phrase is entered by the owner via keyboard. Biometric information may also become available once Card development allows for this feature.

What we can learn from the relevant prior art is that medical data has the need to be readily available to the patients and to the medical treatment teams when needed, but the US patent application No: 2008/0041940 A1, as well as the Walletex product do not cover several highly important and medical markets required operational and security features and capabilities, to make together a fully acceptable and working solution. First due to the sensitivity of the medical records, the access to them should be highly secured and a simple password or even one biometric access permit, as appears at the end of the above cited US patent application second claim, but without any supportive description in the cited patent body itself, is not enough to ensure that a third party with negative intentions will not be able to get access to the user/patient secured medial data. Also this invention card does not have any connectivity and access to mobile phones and especially to the fast growing numbers and types of smart phones, as such an access capability is a real need in the modern living environment, due to the support these phones give to sustain the user's continuous voice and data communication capability with various service providers, as well as medical support and aid services, wherever the user is located. Also, essentially missing in the Walletex device and US application No: 2008/0041940 A1 prior art, is the required capability to measure and sense that a live person is authenticated as the user of the device while the user is actually holding the device in his hands, to avoid the possibility of using the user's access data and even a silicon copy of his fingerprint to fake his presence and get access to the user's secured personal information, this is true not for only medical personal records but also and even more crucial and relevant in the case of getting access to financial records, private data records and classified organizational records, if the user belongs to organization and has a special personal access permit to highly secured information that he needs to carry with him.

It is also highly recommended that when access is given to the sensitive medical records, or other personal data files, when and if the life signs measured results of the devise holder are not normal, to have in the devise the feature of self initiating an emergency call through the user's connected cell phone, or by the user connecting to a host computer, to get a safe access to a remote computer center that will call for emergency medical treatment or an urgent evacuation of the user to the nearby hospital. This requirement of a personal emergency device was dealt by prior art but no practical device was introduced successfully to the markets yet.

Also there is a need to create hierarchy in the access level of permits to the sensitive medical data stored in such a device, as the level of details and amount of medical data on the patient required by the medical rescue team is different and much lesser in content and details than the required access to much more detailed and professional medical data on the patient when the patient has to be professionally diagnosed and treated when he arrives at the hospital emergency room.

Accordingly, there is a need to improve and enhance the access control capabilities to first securely and efficiently authenticate the specific user before giving this user access to sensitive personal data files and then after the user being authenticated in a very high level of security and reliability, to be able to safely and securely communicate and exchange the user's personal secured data with other specific authenticated and pre-approved users and especially with a wide spectrum of registered and approved service and dedicated data providers.

Modern cellular phones, known as smart phones, are being frequently used as personal data storage and access devices, used for such applications as holding the user's phone books and personal data records, but the problems associated with this solution is due to the frequent modern cellular phones models changes and many technical failures of these phones, all that leads to the fact that in many cases critical users' data is getting lost or injured during the process of the devices repeating, maintenance and management procedures as well as the users frequent cellular phones and personal computers changing and upgrading to newer models. A better solution will therefore be to separate the user's sensitive and private data storage and management functions from the cell phone communication and display functions. This functional separation importance between private and personal data storage functions and the communication functions, can be recognized, detected and clarified especially during all the user's sensitive acts of private and needed to be concealed and secured data transfer activities from one device to the other. There is a need in this aspect for holding the user's private and needed to be secured data on a separate highly operational and reliable device, that will be adapting itself and act at the user's portable private data storage device through all the changes, upgrading and maintenance cycles that the user does with his cellular phone and/or personal computer. The user's personal portable data storage device will be able to be connected and then automatically and immediately communicate and interact with the user's new or upgraded cellular phones, in parallel there is a need that the personal device will be able to connect and interact also—with the user's personal computer, as well as with his computer terminal at work, whenever required.

This set of combined capabilities is especially required if the user wants to use the same device to store his own personal mass data base of financial and/or medical records of a highly sensitive level of data, combined with and containing textual, imagery, audio, graphics and figures—covering most if not all the specific user, continuously updating personal data, financial, medical and other modern life management information while ensuring the highly demanding requirements of secured data maintenance.

Regarding these very high security and privacy maintenance requirements and the users sensitivity to the fast expanding technical means and operational trends of exchanging financial related data and making financial transactions through modern computerized communication lines and networks, such as the interment and intranet, there is a need to improve the presently used means and methods of the users interaction through those networks, as they are done today mainly only by simply providing and exchanging the user name and password information as the only security protection means to enable users' access to finance institutions and banks and then it enables users to execute highly sensitive and top security demanding actions such as executing actual financial transactions and stocks trading. It is therefore highly recommended and required to offer more advanced practical new technologies based means and solutions, to provide and support enhanced and improved authentication, communication and data access and remote transactions executions means to provide much better personal financial data exchange, providing enhanced security for sensitive and private information exchange and provide secured and safe sensitive storage and deals executions with better safety and security. The present lack of such improved financial transactions security management solutions, creates the existing markets vast spectrum of mal-opportunities to hackers and criminals to get access to sensitive financial data and the related financial resources of users and organizations and then execute criminal acts on them, related a wide spectrum of misrepresentation based transactions by practically using other users' money. These criminal activities are presently creating annually hundreds of millions of US$ direct damages to the injured users and organizations and consequently also to the insurance companies that insure them through their banks and their credit card companies.

In addition, there is thus a widely recognized need for, and it would be highly advantageous also to have, a dedicated combined computer, Internet and telephony system supporting the multiple authentication, sensitive and very private personal data access and storage of users personal, financial and medical data and then supporting the daily needs for a plurality of said system pre-registered users, to securely communicate and operate their daily highly secured data interaction needs with a multiple of authorized, approved and secured services providers by using the system and adding to it as a critical highly required to security supporting new element by the implementation and the use of said dedicated hand held devices to communicate safely though this dedicated system getting access to said system by the use of said hand held apparatus which has the capabilities of being a combined multi level personal data authenticator and a secured and encrypted mass memory of personal or organizational sensitive and very private data with immediate access to the user holding his very private apparatus wherever he goes.

There is also a need for a highly secured and computerized communication system. Such a system will be open only to pre-registered and enhanced security check approved clients, while the system registered clients will get access to said system only with their system advanced, also pre-registered authentication managing token concept—is expected to dramatically reduce the cases of criminal acts by electronic means to execute financial deals and enable better monitoring and detection any suspicious such deals and quickly and easily track hackers trials to enter that secured system. The system users interaction with the secured system enabled only by using their tokens, will provide each such system user an optimal way to first verify that his entry and interaction with the system is fully authenticated and thus highly protected, then to track his deals as they are processed and to monitor their final execution results before each such a deal is finally approved and finalized by the user.

It is therefore highly recommended and there is a need to have an operational and reliable solution that will support for a multiple of registered users a secured communication and data management needs through a dedicated system and that the system's users will need to use their proposed private personal tokens, operating both as a user combined personal data authenticator and as a secured mass memory personal or organizational portable data storage and handling device, for providing secured and safe accesses to said secured system and to external databases containing sensitive private information of the system users.

SUMMARY OF THE INVENTION

The following embodiments and aspects thereof are described and illustrated in conjunction with systems, apparatuses and methods, which are meant to be exemplary and illustrative, not limiting in scope. In various embodiments, one or more of the above-described limitations and emerging modern user's growing needs have been solved, reduced or eliminated, while other embodiments are directed to other advantageous or improvements.

The core of the present invention is an advanced and highly reliable new generation of physical safe entry and secured access support tokens, in the shape of a small palm size, hand held apparatus, geared to serve and support the user's secured entry needs to modern computerized systems. The invention apparatus has an integrated highly secured personal data communication and management capability, combined with a built-in multi level user's bio parameters measurement and authentication module. In parallel, the invention apparatus fully supports the user's needs for secured data communication capability, to and from a very large data storage capacity, solid state memory module, which is an integral part and is resident within the invention apparatus.

According to the present invention, there is also provided highly secured personal data storage and handling combined system—integrating computers, Internet and telephony components. Supporting the system and its users highly secured personal data handling needs, is the dedicated present invention apparatus, having an integrated built-in, offering multiple security level set of at least two bio sensors, measuring the user's unique personal biological parameters and further providing highly reliable and safe authentication capability, based on the processing of user's measured set of biological parameters. The combined system is enabling for very sensitive personal data files, local memory and remote data suppliers secured access, highly secured personal data exchange and secured personal data storage, by a plurality of users. The system's registered users are communicating and operating through the dedicated system with a multiple of specially authorized services providers, by using the dedicated hand held personal data authenticator apparatus, having a built highly secured and encrypted mass memory for its user personal data storage capacity, thus enabling to upload and down load to and from the apparatus memory updated personal data from the authorized services providers that are pre-registered in the invention system. The apparatus comprises a large memory capacity solid state data storage module, adapted to store the user personal data, while the updated personal data is residing and readily available to the single and unique user. The invention apparatus can serve any user on a private and personal level, or alternatively to serve secured data handling by employees and management of various types of organizations for securely managing all the inter-organization proprietary data, while each such employee is using the hand held present invention apparatus as a high security access key to the company's proprietary information. For the usage of the present invention system, each one of the invention system's multiple users needs to use the invention apparatus in order to provide him or her with secured and safe accesses to the combined highly secured dedicated present invention system.

The existence of such a highly secured communication system, closed for access to the open public according to the present invention, is providing a unique secured and personal data management solution that is only open to pre-registered and enhanced security check approved clients or users. The system registered clients are getting access to the invention system only by using their advanced, also pre-registered authentication managing tokens, which are the invention apparatuses. This new concept is expected to dramatically reduce the cases of criminal acts carried out by penetrating into financial computerized systems, using electronic means to execute faulty financial deals. Furthermore, it will enable better monitoring and detection of any suspicious such deals followed by quick allocation and capture of the financial system intruders who have criminal intentions. Also, it will enable easier tracking of hackers' attempts to enter the secured system and to damage its proper and normal functionality. The system's users interaction with the secured system, which is enabled only by using their personal devices, will provide each such system user an optimal way to first verify that his entry and interaction with the system is fully authenticated and thus highly protected, then to track his deals as they are processed and to monitor their final execution results, before each such a deal is finally approved and finalized by the user. This means that only the authenticated user and no other user will have the possibility to have access to the user's personal files and accounts and to be able do any kind of transaction with, or through them.

In another typical embodiment of the invention, there is a method of operating the invention system comprising the steps of; A) a system user first applying a step of going through a series of multiple level bio personal parameters measurement, processing the measured parameters and then use the results for the user authentication; then B) enabling the authenticated user to manage his personal data, while getting full access to his personal data as well as the user's personal data updating and storage in his personal apparatus. The process is enabled by the user safely connecting through the invention's system with a plurality of such highly secured other system users and for communicating and exchanging secured and encrypted data with a multiple of dedicated, approved and highly secured services providers. By using the dedicated hand held personal data authenticator having an integrated highly secured and encrypted mass memory personal or organizational data module, all integrated within the invention hand held dedicated apparatus, each of the invention system's users needs to use his or her very personal and highly secured present invention apparatus, in order to provide him or her with a secured and safe access to the combined, dedicated secured system for handling and managing a plurality of users secured personal data.

The present invention will create a new safe and secured communication and secured personal data exchange and updating method for private and organizational staff users, which is highly required for supporting the handling, exchanging and storing of mass sizes highly personal and/or organization private and secret data packages, which does not exist today. The system and its operational method is also providing the user with the capability to actively manage a secured safe access to the mass storage data capacity of his highly sensitive and personal data bases and to files stored and continuously updated, by the various registered data and service providers, while using the user's private and secured memory partition within the present invention system memory, structured as very large data storage capacity bank. The user might like to get new data from the system memory and down-load it into the present invention apparatus, acting as his personal data storage device and also decide which part to send to another system user, or to specific approved and highly secured special services providers.

According to another embodiment of the present invention, there is provided an apparatus integrated with at least two special bio sensors and physical parameters measurement means, supporting exclusively and only the apparatus owner and user's personal biological and physical body parameters measurements and authentication, while continuously conducting multiple level bio personal parameters positive authentication process of the apparatus predefined legitimate physical measured parameters. The apparatus is always encrypting and also enabling only one specific user personal data storage, access and data exchange and serving as a mass memory capacity personal data storage by its private user, enabling the device personal owner to communicate and operate through the dedicated system with a multiple of specifically approved services providers by using the dedicated hand held personal bio parameters measured data authenticator and using the built-in and integrated secured and encrypted mass memory personal or organizational highly sensitive and personal data, each of the dedicated systems users needs to use only his/her own very private apparatus in order to provide him or her with a secured and safe accesses to the combined and highly safe and secured system.

According to another embodiment of the present invention there is provided an apparatus that can detect the user's potential emergency situation while analyzing that the life signs measured results of the apparatus holder are not normal, to have in the apparatus the feature of self initiating an emergency call through the user's connected cell phone, or by transmitting a message though the internet when the user is connecting his apparatus to a host computer, to get a safe access to a remote computer center that will call for emergency medical treatment or for an urgent evacuation of the user to the nearby hospital. With the apparatus integrated electronics and communication means the apparatus can be easily and seamless connected to and communicate through a modern cellular phone, or any type of a host computer with the invention dedicated central secured personal data storage and management computer system that will call the emergency units of the nearby hospital based on the location of the sick person which can be calculated from the user's location identification, information that can be derived from the inherent device location identification capability of any modern cellular phone.

To better understand the user's benefits of using the invention apparatus and system, it is required to learn that presently users are frequently losing time and again, their saved personal and important data files, due to mechanical or electrical failures of their electromagnetic driven hard-discs, or suffer from sensitive data files failure or damages related to malfunctions of their personal computers or smart cell phones. Another source for lost sensitive data files, that many time are of a highly personal and important data, is due to software malfunction problems while running on the users' personal computers or smart cell phones, such problems are also frequently created by viruses and Adware infections in the users' computers or cell phones. All these problems can be eliminated, or at least substantially reduced, if the users will use their invention apparatus with its very large solid-state memory data storage capacity, to serve them, as their daily needs supporting backup memory. The invention apparatus is therefore fully supporting of the modern user needs for a highly reliable secured data, solid-state based memory and is protected against viruses by embedded, related, advanced anti-virus anti-Adware software that is frequently updating its DB every time the user is connecting his apparatus to the system, or to the internet through his host computer. Another family of common cases of frequently lost sensitive and important data files is typical to the modern users' habits of frequently changing or upgrading their host computers and even more so, it is common and frequent for them to do model changes with the users' cellular phones. Every time it happens, the users are exposed to losing sensitive data such as a phone books stored in their changed devices. It happens mainly due to the user, or the related cellular service provider, or cell phone supplier not taking enough care and not performing professional and full coverage backup of all the stored data prior to changing the computer or phone. Most users are familiar with the cases that their electronic phone book content was damaged, if not totally erased, when they upgraded their cell phone. Keeping all the users sensitive data, such as his medical records, financial records, credit card access data, phone books, etc on their present invention apparatus wherein the invention system will always automatically create in its own memory a backup file for every file stored by the user on his personal invention apparatus, will support the modern users daily and growing need not to lose their sensitive personal data files in any of the above frequently happening and common system failure and lost data cases.

The apparatus of the invention therefore can integrate all its user's data storage needs in one small and portable device that can store sensitive data in a secured access and encrypted format structure.

There is a growing tendency in the recent years to put all the modern user communication needs in his smart cellular phone but the storage capacity and the safety of the data the user accumulates during his daily life will be much better managed and protected while serving the data in a separate device as described in the invention apparatus motile functions and capabilities.

The modern user could therefore gain the best solution for his daily needs by carrying with him and using on a daily basis both his smart phone as well as the invention's apparatus. Even in cases that the invention apparatus will be lost or stolen, the data in it as well as the user access given by it to other service providers such as the users' financial institutes will be secured and no access can be possible to this sensitive data to any other person rather than the user owning this specific apparatus.

Due to the total data handling high security and safety by using the invention apparatus, it can serve also for processing fully secured financial transactions, while keeping full records of the transaction stages and partners, both in the invention apparatus memory, as well as in the invention system server memory.

In one preferred embodiment of the present invention apparatus, the apparatus is managing personal and secured data and documentation files stored in the apparatus, the apparatus comprising: A) a sensor module comprising a plurality of biometric sensors for reading a plurality of personal biological identification parameters of the user holding the apparatus, the apparatus being uniquely identified with the user; and B) a processing module in communication with the sensor module for processing their personal biological identification parameters and for processing and managing the personal and secured data and documentation files associated with the apparatus user; and C) an authentication unit in communication with the processing module configured to receive and authenticate the identity of the apparatus user by comparing the apparatus unique user's personal biological identification parameters, as read by the sensor module and processed by the processing module, with a pre-recorded set of personal biological identification parameters stored in the apparatus authentication unit; and D) an encryption module in communication with the apparatus processing module for the encryption plus compression and/or decompression plus decryption of the apparatus's user's data files; and E) a memory module in communication with the processing module and the encryption module for the storage of the apparatus's user's data and documentation files; and F) communication and data connection set of means in communication with the processing module for connecting the apparatus with an external device; wherein access to the user's stored personal data and documentation files associated with the unique user is only enabled after positive authentication of the user's personal biological identification parameters by the authentication unit.

In another further embodiment of the present invention apparatus, at least one of the apparatus's integrated pluralities of biometric sensors is a life signs detector, wherein the life signs detector is configured to measure and record at least one of the user's life sign parameters.

Yet, in another further embodiment of the present invention apparatus, at least one of the user's life sign parameters is measured by any of a group of life sign indicators including a body pulse rate measurement indicator, a body $O_2$ saturation level indicator, a body heat measurement indicator, an electro-dermal activity indicator, a body respiration indicator and a physical or emotional stress indicator.

In another embodiment of the present invention apparatus, whenever any of the group of life sign indicators detects a critical level, the apparatus is configured to initiate an emergency call to any of a group of registered emergency centers, and send to the registered emergency centers any of a group of data files containing information associated with the user, including the identification data file of the user, personal medical data file of the user, the measured set of life sign parameters of the user and location of the user.

In another further embodiment of the present invention apparatus, the apparatus has an integrated emergency button in communication with its processing module and the apparatus communication and data connection means module; and when the emergency button is being activated, communication is initiated between the apparatus and any of a group of registered emergency centers, the apparatus emergency call transmitting any of a group of data files containing information associated with the unique user of the invention apparatus, including the identification data of the user, the personal medical data file of the user, and location of the user.

In another further embodiment of the present invention, the apparatus is further comprising an integrated software module that automatically detects the operating system of the computer or cellular phone, connected to the apparatus through one of a group of communicating devices through which the apparatus is connected, and wherein the computer or cellular phone have a keyboard and display units associated therewith, thereby allowing the user to interact with the memory module and with the processing module of the apparatus via the external devices keyboard and display units, whereby the computer or cellular phone is configured to utilize and interact with the memory module, the processing module and the sensor module of the apparatus.

In another embodiment of the present invention, there is provided a method for managing personal and secured data and documentation files of a plurality of unique users, each one of the plurality of unique users having a personal identification unit, uniquely associated with the one user for storing each user's personal data and documentation files, each of the personal identification units comprising: a sensor module comprising a plurality of biometric sensors; and a processing module in communication with the sensor module; and an authentication unit in communication with the processing module; and an encryption module in communication with the processing module; and a memory module in communication with the processing module and the encryption module; and communication and data connection means in communication with the processing module. The method comprises the steps of: a) the sensor module reading a plurality of personal biological identification parameters of the user holding the apparatus; and b) the authentication module comparing the personal biological identification parameters of the user with a pre-recorded set of personal biological identification parameters stored in the authentication unit; and c) if the authentication unit positively identifies the user, allowing the user access to the user's personal data and documentation files stored in the memory module and allowing the user to communicate with other communication means through the apparatus.

In another embodiment of the present invention, there is provided a system for managing personal and secured data and documentation files of a plurality of unique users, the system comprising: A) a system manager for managing and updating personal data of the system plurality of unique users and for communicating with each of the plurality of unique users; and B) a memory sub-system connected to the system manager to store updated personal data of each of the plurality of unique users; and C) a plurality of personal identification units, each of the personal identification units being associated with a unique user, each unique user being registered with the system manager and the personal ID data file of each unique user being stored in the memory sub-system; and D) a plurality of computer hosts and cellular phones in communication with the system manager, enabling the direct connection by the system manager with the plurality of unique users through their corresponding personal identification unit; and E) a plurality of registered emergency centers and a plurality of registered service providers in communication with the system manager, the plurality of service providers including banks, credit card companies, insurance companies, clinics, hospitals and medical insurance companies, government, municipal and utility entities and selected websites frequently accessed by the plurality of users; and wherein the system manager's access to and communication with the personal data and documentation files stored in the personal identification units associated with each of the unique users and to the personal data and documentation files stored by the group of service providers is only enabled after positive authentication of the unique user's personal biological identification parameters by the authentication unit.

In yet another embodiment of the present invention, there is provided a system for managing personal and secured data and documentation files of a plurality of unique users; the system further comprises: a computerized call center configured to receive phone calls or emergency voice and data messages from any of the plurality of registered emergency centers and a plurality of registered service providers and to communicate with any of the plurality of cellular phone and host computers; and wherein the call center is configured to communicate the user's location coordinates to an emergency rescue team and simultaneously the call center is configured to communicate with any of the plurality of registered emergency centers and service providers to receive the user's updated medical data and to transfer the data to the user's personal identification unit.

BRIEF DESCRIPTION OF THE DRAWINGS

The invention is herein described, by way of example only, with reference to the accompanying drawings, wherein.

Figure 1:
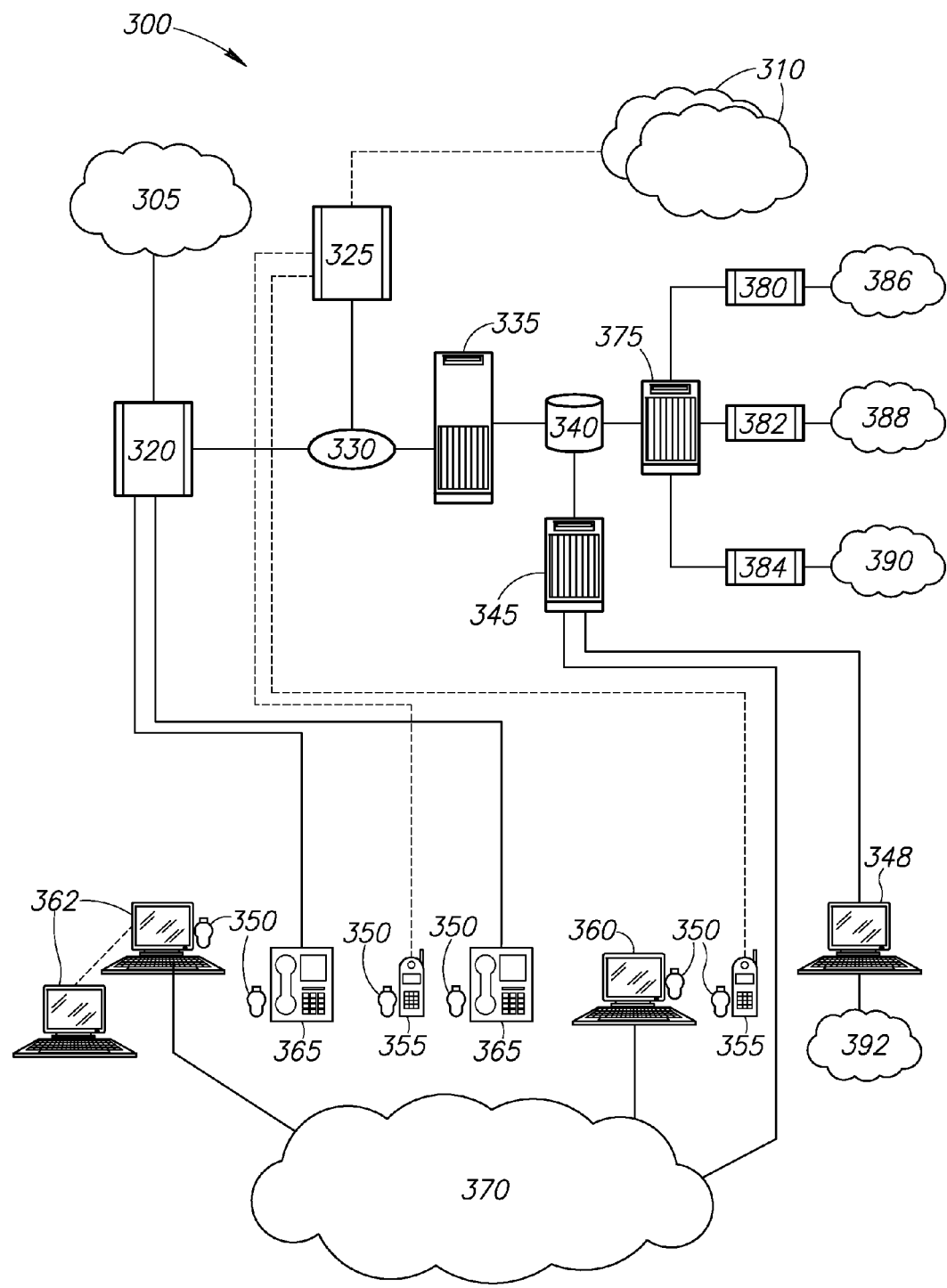
FIG. 1 is a schematic illustration of an embodiment of the present invention related to the invention highly secured personal data dedicated communication and management system.

The present invention will be more fully understood from the following detailed description of the embodiments thereof, taken together with the drawings.

DESCRIPTION OF THE PREFERRED EMBODIMENTS

It would therefore be highly advantageous to have a highly confidential personal data and information management and storage combined solution, both on the user's personal portable device level, as well as the multi-users system level, that enable improved and highly secured personal or organizational data access, storage and management locally and remotely, serving the daily needs of secured and highly confidential data access of private users, as well as for large organizations internal staff.

In the following description, various aspects of the invention will be described. For the purposes of explanation, specific details are set forth in order to provide a thorough understanding of the invention. It will be apparent to one skilled in the art that there are other embodiments of the invention that differ in details without affecting the essential nature thereof. Therefore the invention is not limited by that which is illustrated in the figures and described in the specification, but only as indicated in the accompanying claims, with the proper scope determined only by the broadest interpretation of said claims.

In the following detailed description, numerous specific details are set forth in order to provide a thorough understanding of the disclosure. However, it will be understood by those skilled in the art that the present disclosure may be practiced without these specific details. In other instances, well-known methods, procedures, components and circuits have not been described in detail so as not to obscure the present disclosure.

Unless specifically stated otherwise, as apparent from the following discussions, it is appreciated that throughout the specification discussions utilizing terms such as "storing", "computing", "communicating", "authenticating", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

The present disclosure may take the form of an entirely hardware embodiment, an entirely software embodiment, or an embodiment containing both hardware and software elements. In a preferred system embodiment, the disclosure is implemented in software, which includes but is not limited to firmware, resident software, microcode, and so on.

Embodiments of the present disclosure may include apparatuses for performing the operations described herein. This apparatus may be specially constructed for the desired purposes, or it may comprise a general purpose computer controlled device selectively activated or reconfigured by a computer program stored in the computer.

Furthermore, the disclosure may take the form of a computer program product accessible from a computer-usable or computer-readable medium providing program code for use by or in connection with a computer or any instruction execution system. For the purposes of this description, a computer-usable or computer readable medium can be any apparatus that can contain, store, communicate, propagate, or transport the program for use by or in connection with the instruction execution system, apparatus, or device.

The invention data processing, managing and storage system as well as the present invention apparatus are also adapted for storing and/or executing program codes, may include at least one processor coupled directly or indirectly to memory elements through a system bus. The memory elements may include local memory employed during actual execution of the program code, bulk storage, and cache memories which provide temporary storage of at least some program code in order to reduce the number of times code has to be retrieved from bulk storage during execution. Input/output or I/O devices (including but not limited to keyboards, displays, pointing devices, and so on) can be coupled to the system either directly or through intervening I/O controllers.

The present invention is of a system, an apparatus and a method combining and supporting highly secured data encryption, personal sensitive data storage, transfer, management and handling, carried out by and through the invention computerized, Internet and telephony based dedicated system. Supporting the system and its registered and pre-approved users secured access needs, is the dedicate present invention apparatus having an integral, built in, multiple level set of bio sensors, for collecting and measuring the device owning user personal parameters measured data. The present invention apparatus is used for highly reliable and safe and approved authentication of the device owner. The invention combined dedicated system is enabling very sensitive personal data access, personal private data exchange and personal private data storage by a plurality of similar such pre-approved users, communicating and operating through said dedicated system with a multiple of specially authorized and pre-approved services providers. The system registered users are using, as a highly safe and secured access key, their dedicated hand held devices or apparatuses, which are acting for each such system registered user as his personal data entry authenticator. The invention apparatus has a built-in, highly secured and encrypted mass memory solid state data storage module, both of which reside within said personal or organizational hand held compact size dedicated apparatus. Each of the invention system's pre-approved user's needs to use his specific personal and private present invention apparatus, in order to provide him or her with a secured and safe accesses to the invention combined and highly secured dedicated system.

The principles, the building blocks and functional modules layout and the various functional operations of a system and an apparatus according to the present invention, may be better understood with reference to the drawings and the accompanying description.

Referring now to the drawings, FIG. 1 illustrates the dedicated system 300 related to an embodiment of the present invention, when a pre-approved user is getting an access to the system through any one of the system server based multi-user I/O terminals 362, or through any kind of a host personal computer 360, or alternatively getting the access through a digital landline phone 365, or a cellular phone unit, 355. Secured access to the system is enabled by passing the user through a sequence of at least three bio parameters measurement and authentication process, carried out by the user's apparatus 350.

305 is a typical landline telephone communication network infrastructure, A user with his apparatus 350 of the present invention may connect to a digital smart telephone terminal 365 wherein the landline based digital smart telephone terminal 365, is connected to the system manager 335 through the switch 320, the landline phone network 305 and through a general communication Multiplexer sub-module 330. A user may connect his apparatus 350 to a smart cellular phone 355 and his phone then connects through switch 325 to the cellular infrastructure network 310 and from there through the general communication multiplexer sub-module 330 to the system server 335. Another system user may access the system 300 through the use of his personal apparatus 350 linked to his computer terminal 360 which is connected through the international internet network 370 to the internet communication system server 345. 340 is a mass memory subsystem of the invention system 300, storing and managing the system 300 entire Terabytes order of magnitude size typical memory capacity, containing personal data of all the system 300 users, in a highly secured, protected and encrypted format The entire system 300 controlled and managed by a computerized server manager subsystem 335, is securely transmitting and receiving, processing and storing all the system users set of ID data and secured large memory capacity personal dedicated data to be stored on the 340 storage subsystem. The system is interphasing its activities through the internet infrastructure 370 by using the system website server 345. Multiplexer sub-module 330 enables the central system server 335 communication and data transfer from the landlines and cellular and phone networks 305, 310 through the switches 320, and 325 and multiplexed to the system server trough multiplexer module 330. The system sever 375 is another server subsystem of the system 300 multiple users data management center, which manages the system secured connection and communication through a secured firewall gate protected switch 380, which manages the system secured connection and data exchange communication through the internet, or through multiple dedicated point to point communication lines and channels 386, to a plurality of pre-approved number of government offices, municipalities and other selected secured services and products purchasing providers as well as external personal memory data banks that the system needs to securely communicate and exchange relevant data with them for its registered plurality of user.

Server 375 is also responsible for managing the communication through a secured firewall gate protected switch 382 which manages the system secured connection and communication through the internet, or through multiple dedicated point to point communication lines and channels 388, with a large number of registered banks and insurance institutes and other financial institutes that have accumulated and continuously updating relevant highly secured personal data related to each of the system multiple users and that the system 300 needs to communicate with and download and upload data relevant to each of the system 300 registered multiple number of users.

Server 375 is also responsible for managing the communication through a secured firewall gate protected switch 384, which manages the system secured connection and communication through the internet, or through multiple dedicated point to point communication lines and channels 390, with a large number of registered hospitals, medical insurance companies, clinics, medical testing laboratories and medical imaging centers that generate and have accumulated and continuously updating relevant highly secured medical personal data about each of the system users, that the system 300 needs to communicate with and down load and upload data relevant to each of the system 300 registered multiple number of users.

System 300 has an emergency management integrated section that enables any of the system's registered users to immediately connect with the system in an emergency case. Connection is enabled by the user when pressing on an integral dedicated emergency button the user has in his apparatus 350, when the apparatus 350 is connected to a cellular phone 355 or to a host computer 360. In such a case, a connection sequence is created between the user apparatus 350 and the system server 335'; the system server 335 then identifies this connection as an emergency message and directs the emergency message to emergency server 345. The emergency message includes a continuously updating medical and user ID details data package stored in the apparatus 350.

From the emergency server 345 the user emergency message will be forwarded to the system's special controls and emergency management center 348, this emergency center will be regularly managed by human operators for further handling and best managing the user emergency situation. The center 348 may then select and call through the emergency management network 392 the medical rescue team which is most relevant and geographically closest to the user, as well as the final destination hospital or medical treatment center and provide the emergency rescue team and the hospital with the user name and ID data, his present geographical location and all the personal and medical data files of the user that are stored in the system memory related to this user. The hospital will receive the specific user's full set of relevant health and medical related data files stored in the system memory, while the rescue team will get only the emergency data package stored on the user's apparatus 350. The emergency center 348 will also be able to work automatically without human intervention and will in case of no human presence at the emergency center 348, contact the national medical emergency services phone number and read to them in a synthetic voice, for example, the content of the emergency message created and generated by the user personal apparatus 350 and in parallel will transfer the same emergency message content to the emergency messages reception section at the website of the national emergency center. In the case where the user connects to the system though his cellular phone, the invention apparatus detects if the connected cellular phone has a built in GPS unit. Since GPS is becoming a very common module in most smart phones, then the apparatus controller may read from the cell phone the local position of the user, in the emergency case, and will be able to transmit the user's present location data to the system emergency management center 348 for further notifying this information to the rescue units.

Figure 2:
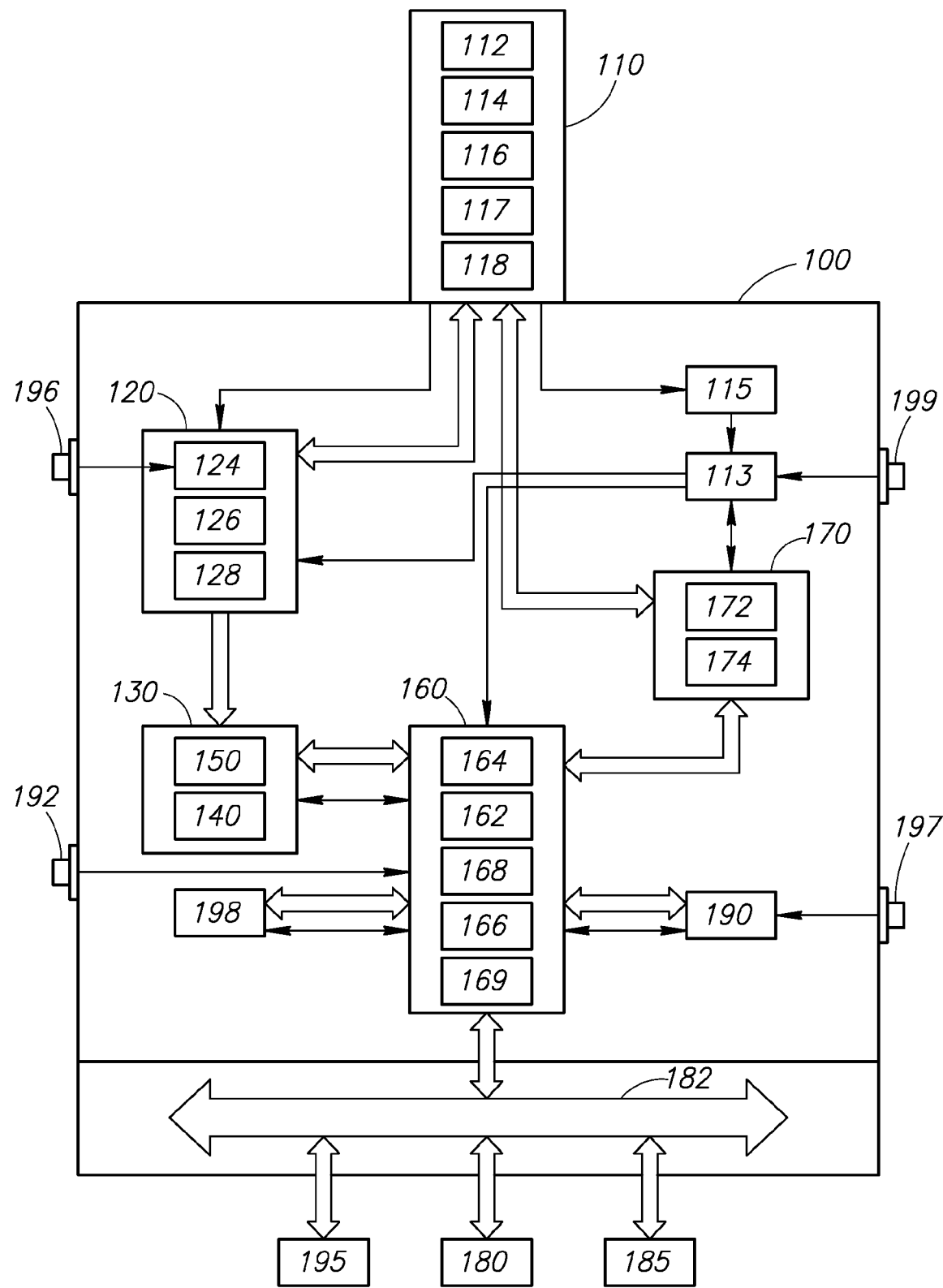
FIG. 2 is a schematic illustration of an embodiment of the present invention block diagram related to one of its possible conceptual modular structure and the internal sub-modules layout and functionality of the present invention apparatus.

A possible block diagram layout configuration of the present invention apparatus and the related apparatus's user operation in using the apparatus for secured data communication and storage, in a preferred embodiment of the invention apparatus is shown in FIG. 2.

The apparatus 100 is comprised of at least 5 different main and essential sub modules and may be also comprised of any combination of additional optional five sub modules, each module providing the associated part and special functionality features of the present invention apparatus, special features and capabilities. Apparatus 100 preferably is compact sized and is light in weight as possible, ergonomically designed to be easily held and operated by and within one palm of any potential user and easily attached to the USB or a similar data communication port of a host computer, or of a cellular phone. To support the need for reliable operation of the apparatus 100 in daily use for at least several years, it may be also designed to be highly shock and vibration resistant on the same level of durability that modern cellular phone have, yet to be water resistant and to have high temperature, industrial level, endurance capability. For special users in heavy duty applications, the apparatus may also be built in and be waterproof and will be in such cases also very durable to wide amplitude and range of vibrations and shocks, in a wide range of operational and storage conditions.

Module 110 is the apparatus host terminals, cellular phones and other accessories connection support. Module 110 may include any combination of standard USB type and/or non standard data connectors 112 extended out of the of the apparatus case, a wireless Bluetooth communication interphase 118, a RF medium to short range communication interphase 117 and another in-room IR communication interphase 114 data communication interphases with the outer world, that will support quick and affordable non-contact communication, as well as physical connection of the invention apparatus 100 to any computer terminal, mobile phone devices, ATM and vending machines Etc. Such connectors could be USB data connectors 112 integrated in most standard PC computers and laptops and mini USB, or compatible Mini USB data connectors 116 that one could find in all modern smart-phone cellular phones models. The preferred embodiment apparatus shown in this figure has in the terminal connection unit 110 a Bluetooth wireless communication interphase circuit 118 to enable easy and quick data communication and non-contact short range connection to most market's available cellular phones, to some models of laptops and notebooks that have built-in wireless Bluetooth data communication capability and through available Bluetooth USB plug-in, token/dongle type devises, that enable contact-less data communication with all modern PC and laptop/notebook, types of host computers.

Module 120 is the module containing the apparatus authentication dedicated set of biosensors, wherein in the preferred embodiment demonstrated in this figure, the apparatus includes two biometric sensors with different optics that are based on imaging. Sensor 124 is an imaging camera based sensor that images the user specific face pattern or the user's eye iris, and generates a set of parameters that are specific to the user face pattern, or his iris structure and pattern, and are based on processing and compressing the specific user face or eye iris pattern and colors. The imaging sensor 124 may be a conventional two dimensional Black & White solid-state miniature camera, or a similar color camera, or a 3 dimensional imaging camera that is based on the integration of either two perspectives images 3-D conventional imaging components, or laser holographic imaging of the user's 3-D face pattern. Activation of camera sensor 124 is carried out by pressing camera on/off button; the user presses the button 196 whenever he needs to pass through an authentication process. The camera will operate until it grabs a good quality image of the user's face features, to enable processing of the user's unique face structure parameters. After grabbing the user's face image the camera's power is shut-off, in order to save the apparatus's battery power. If the camera does not shut down when needed, the user can always shut the camera down by pressing again button 196.

Imaging sensor 126 is one or more fingerprint sensors that image and analyze the fingerprint of one or two of the user's fingerprints. Sensor 128 is biological life sign detection and measurement dedicated electro optical sensor that through projection of a diode laser illumination on the user's holding palm internal blood vessels and the detection and processing and measurement of the back reflected light signal from these blood vessels, it measures the heart pulse rate of the user, while holding the apparatus in his palm and also measures the oxygen ($O_2$) content in % in the user blood at that moment. These two sensors are based on a single electro-optical unit that projects laser or LED diodes light on the user palm and then screens and analyses the modulation of the back reflected light to calculate and monitor the amount of oxygen in user's the red blood cells and the pulsating fluctuation in his blood vessels that due to the user heart bit rate. If the user is in a stress state like the situation that he is forced to use the device by another person, then his blood pulse rate will be out of normal range and the apparatus will not enable the authentication process positive termination unless the heart bit rate will be normal again and for at least a predefined time period. The sensor 128 will be an adaptive sensor so it will measure the heart bit rate every time the user will use it and will make a smart moving average of the heart pulse rate results change in time, to act as an adaptive threshold specifically adapted to the apparatus's personal user typical or normal heart bit rate. The $O_2$ content part of this sensor will measure the well being of the user and will stop the authentication process if there are any abrupt changes in the measures $O_2$%, as well as stop the authentication process if the measured $O_2$ level is not in the normal range of 90-100% oxygen content.

Another possible embodiment of the present invention apparatus may contain alternative life parameter measurements indication by one or more sensors that can replace, or be added on top of sensor 128, to detect the user's evidence normal or abnormal emotions, these are called Affect Sensors. They are used to detect information related to emotional, cognitive, and physical arousal of a user. These sensors are coupled with algorithms that are specifically designed to distinguish and classify patterns associated with the user emotional states. Among this group the apparatus may include sensors that can detect physiological signals such as electrodermal activity and respiration.

Electrodermal activity may be measured by a skin voltage sensor, like the Biowave, developed by the company Infusion Systems Ltd. from Quebec Canada that developed a sensor that captures the skin surface voltages.

Another similar sensor is the Skin Conductance (SC) sensor Flex/Pro Sensor SA9309M that is sold by the US Company WorldWorks, Unlimited, Santa Rosa, Calif. 95404. This sensor measures the skin's ability to conduct electricity. A tiny electrical voltage, so small it is not felt by the user, is applied through two electrodes, usually connected to two fingers of one hand, in order to establish an electric circuit where the user becomes a variable resistor. The real time variation in conductance, which is the inverse of the resistance (an alternative measure of the Galvanic Skin Response), is calculated, changes in SC reflect changes in the activity of the user sympathetic nervous system. As a user becomes more or less stressed, the skin's conductance increases or decreases proportionally. Skin conductance, galvanic skin response and electro-dermal response (EDR) are different terms for similar physiological measures. The standard measurement unit for conductance is called Siemens. Skin conductance is measured in micro-Siemens. Some biofeedback systems display skin conductance in micro-mhos.

Module 130 is a hardware and software combined module, containing the apparatus sub module 140 for carrying out the user final authentication by first digitizing and processing the output of module 120 set of sensors and then combining the measured results of the multi sensors tests output to a final "go/no-go" user's authentication result. Positive authentication result is only achieved when positive results are derived from at least three biological parameters measuring sensors 124, 126, 128, as detailed herein. This module also includes a sub-module 150 that stores a set of data files that are defined by the user as private, yet non-secured, so they may be stored in the original digital format without encryption. These data files may store the apparatus owner full name and his national ID number or National Security number, passport number, driver license number, date and country of birth, address and any additional similar information that appears in the user various cards and his picture. This picture and also other information, such as height and eye color, for example will be sent as a highly reliable patient identification to the rescue team, in case of an accident. It may also include the apparatus owner's private main medical data, which is needed in case of an emergency, for initial medical treatment. The data may include medical data such as the user's blood type, sensitivity to medications, chronic diseases, last standard blood tests results and the user recent medical treatments data of the apparatus 100 owner, for example. It may also include, name and contact details of a selected relative/contact person to be called by the rescue/medical team in case of emergency and the contact details of his private doctor in case the user has a chronic disease, such as heart or a gastro problems.

The medical emergency team may have a special token that can be connected to the USB plug 112 in the apparatus 100 and when needed and the emergency button 192 is pressed, then that apparatus 100 stored emergency data, stored in sub module 150, will be automatically downloaded into this emergency team special token together with the user's picture to verify that the user's apparatus belongs to this specific user. Emergency button 192 may be also pressed by the apparatus 100 user himself, in case he does not feel well, or if he is involved in an accident. Whenever emergency button 192 is pressed by the user, while holding the apparatus in his hand, the user is being authenticated by the apparatus 100 controller module 160. At this stage the user's name, his ID data and the user emergency medical data, as stored in memory module 150, are all sent to the invention system server and from there to the emergency control room unit 348.

From there the emergency call will be forwarded to various medical units through a network of dedicated communication lines and the internet network infrastructure. Using the system emergency control room and the related user's emergency situation maintenance service will enable a reliable and quicker service for the user or the control room manager to help the emergency rescue team and provide first medical aid and other types of help from a spectrum of medical assistance units.

When the apparatus 100 needs to communicate with the outer world through a cellular phone 355 or a host computer terminal 360, it first sends the command to connect the user apparatus to the Internet. Then the apparatus 100 sends to the selected service provider website, the data needed to connect the user to this specific website, such as the specific site user's registered user name, his password and if needed also an account in case of a financial institute or member number. When connected to the service provider website, in some cases the apparatus might be requested by the service provider website manager to provide another data file that identifies the legitimate registered user specific apparatus by transferring a file containing the ID unique embedded numbers of the specific apparatus and its user ID data. If needed and requested, this additional data file may also include the user's national ID card number, and/or his national security number and/or it passport or driving license number, so that the receiving entity such as a medical institute or a bank can compare this data to a reference data stored in its memory before it starts secured personal data exchange with the apparatus and its user.

Module 160 is the central controller and data processing unit for apparatus 100. Unit 160 is an advanced generation low power CPU processor such as the ARM. The ARM is a 32-bit reduced instruction set computer (RISC) with instruction set architecture (ISA) offered by ARM Holdings, a technology company headquartered in Cambridge, UK. The relative simplicity of ARM processors makes them suitable for low power applications and a preferred CPU solution in mobile and portable electronic devices.

Module 160 will control the operation of all the apparatus sub-modules, but also will do through sub-module 172 the encryption and the deciphering data processing work carried out by memory sub-module 172 upon storage and retrieval processes of all the highly secured user's personal data files, stored in the secured mass memory sub-module 174. Module 160 will also make the required data processing on the output of the apparatus integrated at least 3 bio sensors, done through sub-module 140. Module 140 will store the registered user's original, initial registration step, bio sensors measured output for reference and module 140 will also process the authentication parameters output data formatted reference file from the sensors reference output. Module 160 will create, via the authentication sub-module 140, the authentication process and the related decision required to enable operation of the apparatus 100 only by the legitimate owner and user of said specific apparatus. Module 160 also includes sub-module 168 that acts as the emergency button 192 interphase circuits that triggers the processing of module 150 stored data, that creates and sends a user's private and dedicated medical emergency situation data package when needed to the emergency services and rescue teams and to the system emergency center 348.

Module 160 also includes an embedded SW sub module 162 that has the function to support the apparatus 100 automatic adaptation required to enable two way communication with all commonly used Operating Systems (OS) software packages, resident on the external host computer or on the cellular phone that the user has linked his apparatus 100 to. This automatic adaptation, by the apparatus's controller unit 160 for quick adaptation to the external CPU OS needs, is highly required in order to operate with the host or cellular phone in case of a simple apparatus data updating and management process, or to communicate with other users or systems, in most cases through the invention secured communication and personal data storage and management system 300; required in most cases to communicate with the outer world. Such OS automatic identification, interphasing and communication SW package resident in sub-module 162, can automatically recognize, adapt itself and communicate through data connection sub-module 110 with any host computer running on Microsoft's Windows, or Mac OS, or Unix OS, resident in such host computer, or for interphasing with the OS of a cellular phone, such as Symbian, or Android, Embedded Linux, Palm, or Blackberry OS, all commonly used in advanced cellular phones, also called smart phones. RIM Operating Systems offer a number of services to application programs. Applications access these services through application programming interfaces (APIs) or system_calls. By invoking these interfaces, the application may request a service from the Operating System, pass parameters, and receive the results of the operation. In cases where the host computer is one typical terminal 360 in a cluster of a multiple array of terminals of large system, such as Unix-like systems including http://en.wikipedia.org/wiki/Free_software free Unix variants such as GNU/Linux and BSD, the user interface at the host side is always implemented as software that runs outside the host Operating System. In some other OS like Windows, the Window manager can be part of the operating system itself.

While servers generally run Unix or some Unix-like operating system, embedded system markets are split amongst several operating systems, although the Microsoft Windows line of operating systems has at this time almost 90% of the client PC market, other such case OS can be Mac OS, or Google chrome OS, or other host type resident OS.

While the apparatus controller unit 160 can automatically detect and adapt itself to communicate and interact with all commonly available Operating Systems managing the host or cellular phone that apparatus 100 is connected to, unit 160 also can interphase with the external host computer or cellular phone devise it is connected with, in a way that regardless of the type of host computer or cellular phone the apparatus 100 is connected to. The displayed screens and the apparatus 100 supported operational functions selection menus that are displayed on the host computer monitor or the cellular phone display screen may all look the same and function in the same way.

The present invention apparatus 100 holds in its controller's operational memory, a dedicated software package 164 that is capable of identifying (by the SW module 162) the Operating System of the host computer or the cellular phone apparatus 100 to which it is connected to. Then SW package 164 automatically converts all the prepared and stored interaction screens and menus of the apparatus 100, to fit the host computer or cellular phone detected operating system and the dedicated SW package 164 automatically makes the corrections and required adaptations in the apparatus 100 to host or Cellular phone interphasing SW modules, so that the displayed screens and menus on the host or cellular phone screens, will always look the same to the user while viewing the host computer or the cellular phone screens, regardless to the specific host or cellular phone type and model the apparatus 100 is connected to by the user.

Mass memory secured data module 170 includes the encryption SW and hardware sub-modules 172 that will encrypt and compress the user's highly sensitive private and personal medical and financial data files, as well as carrying out the counter operations of decompression and deciphering of the sub-module stored secured personal data when needed.

In order to ensure that the encryption process will be highly immune to potential hackers trials to break the encryption code and read the personal highly secured data of the apparatus 100 user, the encryption keys required to encrypt and decipher the secured data in sub-module 174 will be stored in a separate special memory partition located in the other memory module 150 under a secured memory storage structure and in a way that it will be very hard for the hacker to allocate them and use them when he might try to break the encryption codes of the data stored in the secured data memory sub-module 174. Sub-module 150 is part of the memory and authentication larger module 130.

The apparatus user sub-module 174 is a very large data storage medium based on solid state memory chips, preferably but not exclusively of Flash memory type. An alternative solution for the sub-module 174 may be a new generation of erasable multiple-use memory device which is the Nano-RAM. The Nano-RAM is a proprietary computer memory technology from the company Nantero. It is a type of non-volatile random access memory based on the mechanical position of carbon nanotubes deposited on a chip-like substrate. In theory the small size of the nanotubes allows for very high density memories. Nantero also refers to it as NRAM in short.

Typical storage space required in sub-module 174 will be in the range of 16-256 Gigabyte data storage capacity and may be better configured with advanced memory components, such as NRAMs, to have data storage capacity of up to several hundred Gigabytes and in specific users requirements can be upgraded to up to several Terabytes of compressed data storage capacity, while still maintaining a very compact and minimal physical volume, as required for a compact size hand held device, such as apparatus 100.

Sub-module 190 is a RFID receiver and transmitter unit that enables remote identification of the apparatus and its user by other systems which have integrated RFID units. Sub-module 190 may support the use of apparatus 100 as an electronic contactless key, to enable safe, secured and easy access through secured entrance gates and doors and in other cases also enables, by pressing the RFID button 197, the use of apparatus 100 for safely and remotely opening and locking private homes and offices keyless RF operated door locks and cars.

Figure 9:
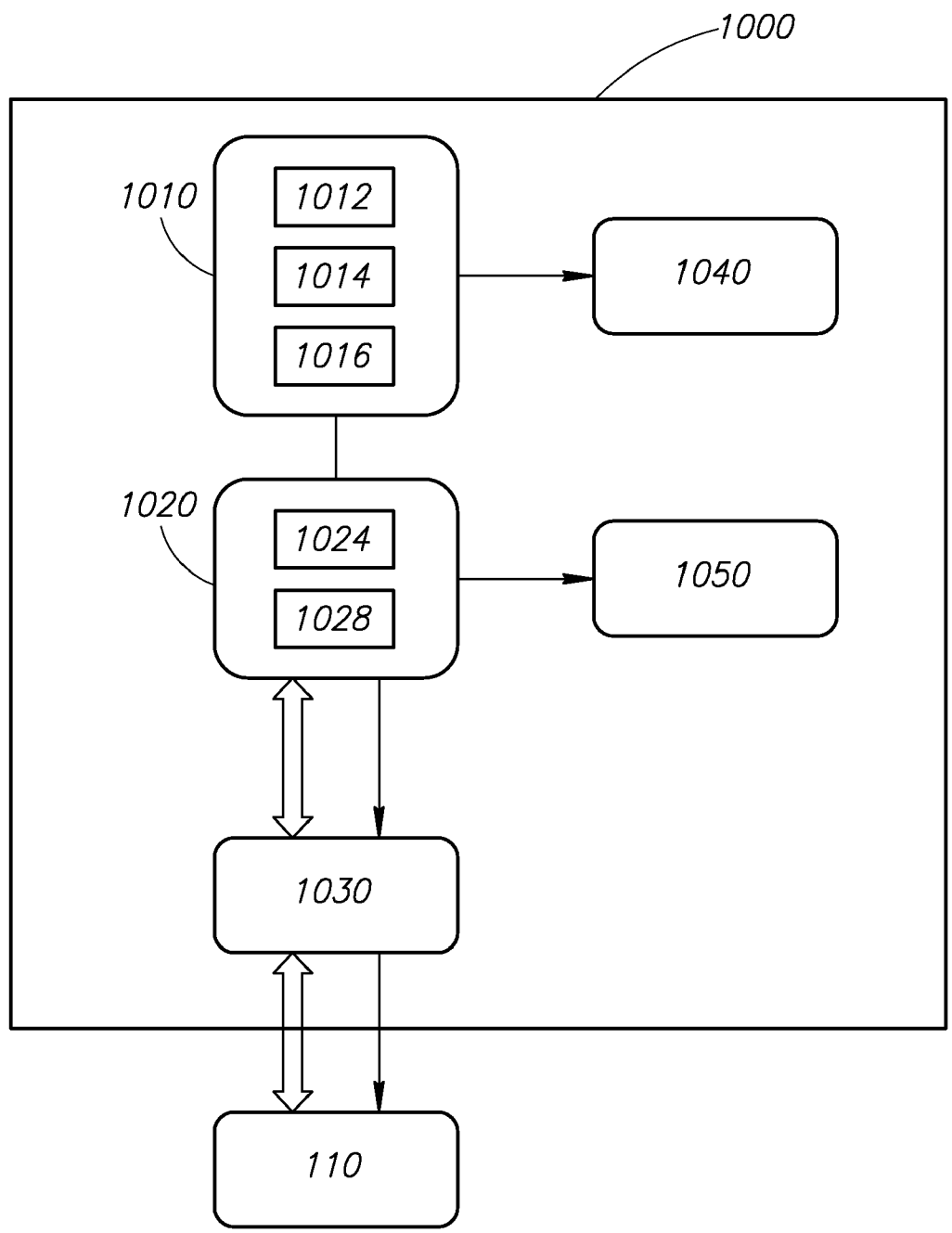
FIG. 9 is a schematic illustration of one embodiment of the present invention related to the invention dedicated device for charging and data backup operations of the invention apparatus, the device is demonstrating one possible conceptual modular structure block diagram and the internal sub-modules layout and functionality of the present invention device functional capabilities.

Sub-module 198 is a RF Transceiver unit that can receive encoded RF commands from a remotely located apparatus's dedicated charger and data backup unit 1000 described in FIG. 9. Unit 1000 is usually located at a short to medium distance from the apparatus 100. Sub-module 198, once triggered by a coded RF signal coming from the charger and data backup unit 1000, will operate an electronic sound buzzer circuit 166, located in the controller module 160, to enable quick and easy finding and allocation of the apparatus 100 by the apparatus's personal user.

Units 115 and 113 together, may create the combined electrical power source and multiple voltage electronic power supply sub module of the apparatus 100. Unit 115 may be lithium, NiCd, or other dry cell rechargeable battery situated in a battery housing that can be opened to change the battery if needed. Unit 115 may also connected to the terminal 110 through which the battery 115 recharges when the connector integrated in module 110 is plugged for charging and memory backup into the dedicated device 1000. Power supply unit 113 may provide all the required voltages to the electronic module 160 and the memory modules 130 and 170; also it may provide the voltages required to the sensors unit 120 and to the RF transceiver and RF ID units 198 and 190. Apparatus's main on/off switch 199 controls the on/off status of the power supply unit 113 operation and though it the on/off operational status of the entire apparatus 100.

Apparatus 100 may include, in another preferred embodiment, an optional additional GPS module 180 that connects to the controller module 160 through its data bus sub-module 182, wherein the GPS optional module 180 will enable apparatus 100 to accurately measure and calculate the momentary precise geographical position of the apparatus and its user and in case of emergency, when the user will press on the emergency button 192, or alternatively when the apparatus integrated bio sensors module 120 detects an emergency case based on a medical abnormality state of said apparatus user, such as if the user's pulse rate as well as his blood oxygen saturation level are both far out of normal range and while the user holds the apparatus in his palm and the apparatus 100 is connected and communicating with the system 300 though the user's cellular phone, or connected to any host computer that is connected to the internet network. In this case, the emergency updating data package stored in a dedicated processing and storage sub-module 150 managed by controller module 160, will be transferred to the system server 345. From there, the emergency case data will be forwarded to the system's special control and emergency management center 348 for further handling of the user emergency situation notification and then the emergency management center 348 will select and call through the emergency management network 392 to the most relevant and closest to the user medical rescue team and provide the team with the user name and ID data, his present geographical location and all the personal and medical data file of the user that is stored in the system memory related to this user.

In case the system 300 does not respond, then the apparatus's controller 160 will automatically dial through the connected cellular phone, and get connected with the national medical emergency call center number and, in a synthetic voice generated by the controller 160 special synthetic voice circuit, will indicate the geographical position and the emergency situation stored medical data package of the specific user. Alternatively, or in parallel, in case that the apparatus 100 can be connected to the internet network by the user through a host computer, or through a smart cellular phone, the apparatus will then connect through the host or phone to the website of the national medical emergency services and will send to this website an emergency case notification and a data file including the user name and ID data and all the personal and medical data file of the user that is stored in the non encrypted and open to access memory sub-module 150 of the user apparatus 100.

It should be noted that for allocating the apparatus and its user, in case of an emergency medical situation of the user, the user location can be alternatively calculated and transmitted to the user apparatus 100 by the cellular service provider in case the user is connecting his apparatus 100 to a cellular phone 355. These cellular phone allocation services are offered today by most cellular services providing companies. Such a connection was previously explained in the section covering system 300 structures and operational method. Therefore the GPS sub module 180 in apparatus 100 is optional in cases of a need to get more precise user's geographical allocation data and might be integrated into apparatus 100 only for users who want a better positional accuracy indication to the rescue and medical teams, in case of emergency to the apparatus 100 user.

Apparatus 100 may include in its modular structure two additional optional modules as well as the GPS optional module 180. One additional optional module 185 may be a display and touch screen optional module 185 that enables a user using the apparatus 100 to communicate with the remote system 300 and to get access and communicate through menus and data typing through the internet with external services providers without the need for the user to have an external cellular phone or to connect to a host computer. Touch screen module 185 will communicate with the apparatus's controller module 160 through bus 182 and interphase sub-module 169 An optional third module 195 is a cellular modem acting as the apparatus data communication module that when connected to the apparatus's computer controller module 160 through data bus 182 and the interphase sub-module 169, it will support the full scale operation and the execution of all the apparatus 100 functions without the need for connection to an external host computer or to connect the apparatus to a cellular phone. Integration of optional modules 195 and 185 might have some drawbacks such as the need to have an apparatus 100 in a much larger size, it will have more power consumption and shorter battery charging life cycle, it will have higher price and operational costs as it functions as a cellular phone and needs to be registered at a cellular company and what is more important is that it will have very limited user interaction functionality due to the small size of the apparatus display and visual keyboard.

Figure 3A:
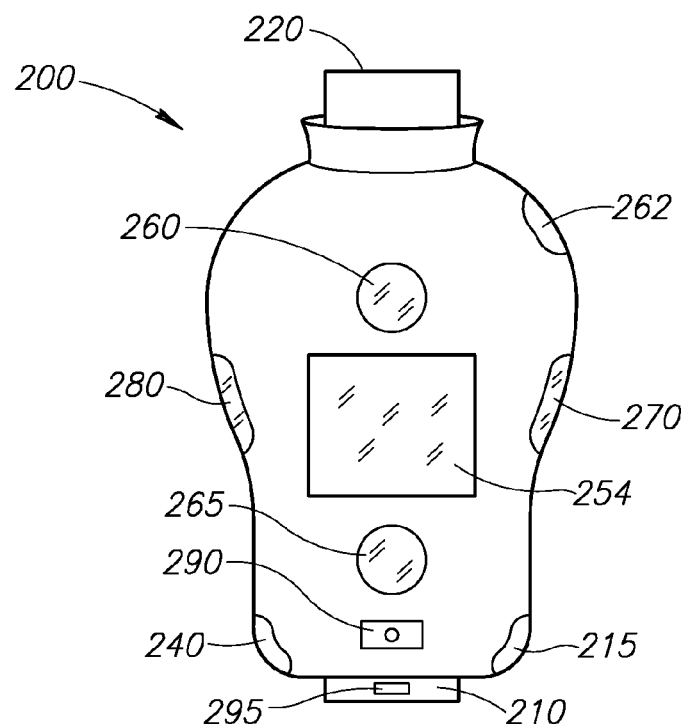
FIG. 3 is a schematic illustration of an embodiment of the present invention apparatus, related to a conceptual external device look and functionality of one embodiment of the present invention apparatus.
Figure 3B:
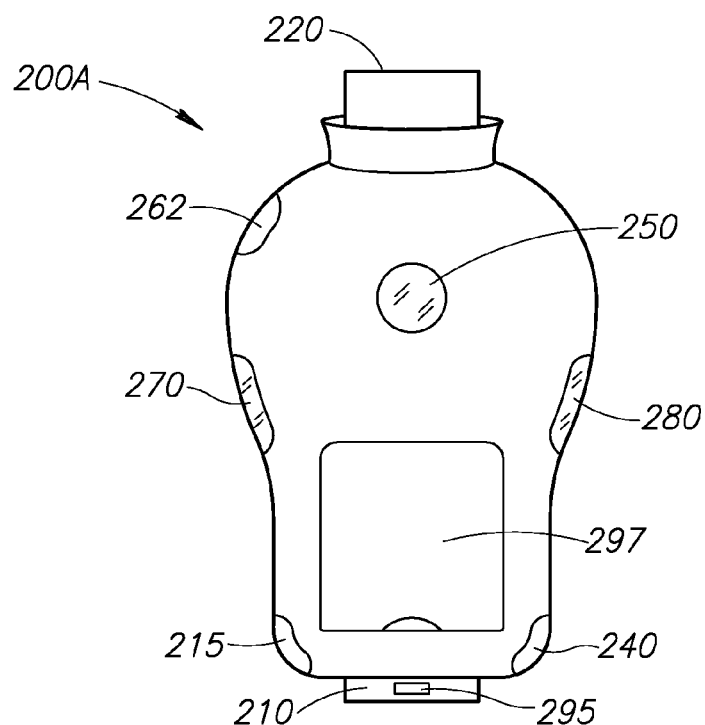

Another embodiment of the present invention apparatus, demonstrating one preferred embodiment of the invention apparatus, related to the apparatus physical structure, design and look, demonstrating also its related I/O interphases and its multiple sensors integration preferred solutions as integrated in the apparatus 100 specific embodiment design and structure, are shown in FIGS. 3A and 3B

Apparatus front view 200 as appears in FIG. 3A, shows the front side view of a preferred embodiment and apparatus view 200A shows the rear side view of the same embodiment of apparatus 100.

Element 210 in the apparatus 100, as seen on the front view 200, is an extending magnetic card thin profile element, that enables interphasing the apparatus 100 with magnetic cards readers/writers such as those one can find in any shop, or gas stations or ATM machines. Magnetic card element 210 is designed to be normally concealed within the apparatus 100 case and can be extended out of the housing by the user for easy interphasing to and interaction with any magnetic card reader and then exchanging data and further enabling the execution of a transaction through any ATM machine or any purchasing point magnetic card reader. The extension of the magnetic card element out of the apparatus 100 case can be carried out by the user fully pulling out and extending this element 210, only if first it is enabled by the apparatus controller 160 in FIG. 2, by releasing in apparatus 100 an internal electronically operated safely locking pin, situated inside the apparatus 100 housing, The safety pin is released by controller 160 in FIG. 2, only when the original apparatus 100 owner and user is actually holding the apparatus in his hands, and only after the user has been recognized and positively authenticated by the apparatus controller 160 while comparing the measured bio sensed set of parameters of the apparatus present holder, to the set of parameters, stored in the apparatus's authentication memory sub-module 140 in FIG. 2 for the relevant bio sensed parameters of the apparatus 100 legitimate user and owner.

Each of the two elements 260 and 265 represents the dual selectable, user's personal bio ID sensor units, comprising the group of sensors including but not exclusively, an imaging sensor, a fingerprint scanning and analysis sensor, a user iris reader sensor, and a 3D holographic or laser scanning imaging sensor. In the preferred embodiment shown in apparatus 100 front view 200, the aperture 260 belongs to a camera that takes high quality still pictures of the users face and then process it to set of parameters that have very high reliability in exclusively characterizing the user by a set of personal ID characterizing parameters that are related to the user face structure and the measured distances between his main face elements. Element 262 is the ON activation button of the sensor 260, to save apparatus 100 battery power consumption, the sensor 260 deactivates itself whenever it has accomplished a satisfactory result of grabbing the face image of the user.

The aperture 265 in the described apparatus front view 200 embodiment belongs to an electro-optical sensor that takes high quality images of the user's eye iris and its specific patterns and colors, and then processes it to set of parameters that have very high reliability in characterizing the user related to the specific user's eye iris structure and colors.

Element 220 in the apparatus 100, as seen in front view 200 is an extendable or fixed USB connector or any similar industrial level available data access connector that can be used when the user wants to connect the apparatus 100 to his host PC computer or to connect to any multi-user computerized server based system, using a computer terminal that has data interphasing capability with a data connector of any kind integrated into the computer terminal. Element 295 in the apparatus's front view 200, is a fixed or an extendable mini USB data transfer connector or any other industry data mini size connector equivalent, that is integrated into all modern cellular phones, a connector that can be used when the apparatus 100 user wants to connect to the outer world through his cellular phone.

Element 262 is the on/off switch of the camera 260 unit. Element 280 in this preferred embodiment of apparatus 100, is a third biosensor unit that executes a fingerprint scanning and analysis of the user's thumb finger if he is right handed and naturally holding the apparatus 100 in his left palm.

Element 270 in this preferred embodiment of apparatus 100, is a forth optional biosensor unit that executes a second fingerprint scanning and analysis of the user's left hand middle finger, if he is right handed and naturally holding the apparatus 100 in his left palm.

Element 254 is an optional back lighted LCD display and touch screen unit, that can be integrated to the apparatus 100 for users that do not own a smart phone and do not have easy access to a host computer and they need to interact with the apparatus 100 controller and review the menu screens and communicate with the system 300 servers as well. In such a user demand, the apparatus 100 optional configuration should support and be supplied with the optional cellular modem 195 (in FIG. 2) that enables the apparatus 100 to function also as a simple cellular phone, while dialing out and interaction with the apparatus will be carried out by the touch screen functional capabilities which are a part of this display unit option 254 for apparatus 100 (external view 200).

Element 290 in front view 200 of this apparatus 100 preferred embodiment is a general on/off switch of the apparatus 100 which has an integrated ON status indication red light emitting LED.

Element 240 are press button functions for the apparatus 100 integrated RF sub-module communication and RFID activation switch, for remotely operating and securing operations such as contact-less access to secured sites, communication with advanced contact-less ATM machines, smart cards readers and RFID operated door locks and car doors and/or ignition switches.

Emergency button 215, is used for pressing by the user in case of emergency, in such a case apparatus 100 is connected and communicating with the system 300 if the user is connecting his apparatus 100 to his cellular phone, or if he connects his apparatus 100 to any host computer that is connected to the internet network.

Apparatus 100 back view 200A shows the rear side view of the same preferred embodiment of the apparatus 100 shown front view 200.

Element 250 in view 200A is the sensing aperture of the life signs detection biosensor to sense and indicate the real-time operation of the invention apparatus 100 by a living and healthy human operator. This sensing function is carried out by a dedicated sensor or combined set of sensors, which may be selected of a list of possible life signs indication biosensors and will be one or more possible bio-sensors selected from the group containing at least a body temperature measurement sensor, a body pulse rate measurement sensor, a body $O_2$ saturation level sensor, an electrodermal activity sensor and a respiration sensor. The preferred embodiment shown in apparatus 100 view 200A behind aperture 250 may have a dedicated integrated life signs measurement sensor module, made of such combined and integrated two life signs indication dual channel electro-optical sensor, that measures and performs simultaneously both human body pulse rate in one channel and blood $O_2$ saturation level in the other channel, which is offered by the company SPO Medical Equipment Ltd., of Kfar Saba, Israel (www.SPOmedical.com)

Element 297 of view 200A is the external opening lead and cover of the rechargeable battery housing of the apparatus 100. The rechargeable buttery in the housing can be replaced or checked by removing the cover lead 297.

While the invention apparatus has been described with respect to a limited number of embodiments, it should be appreciated that many variations, modifications and other applications of the invention apparatus may be made.

Figure 4:
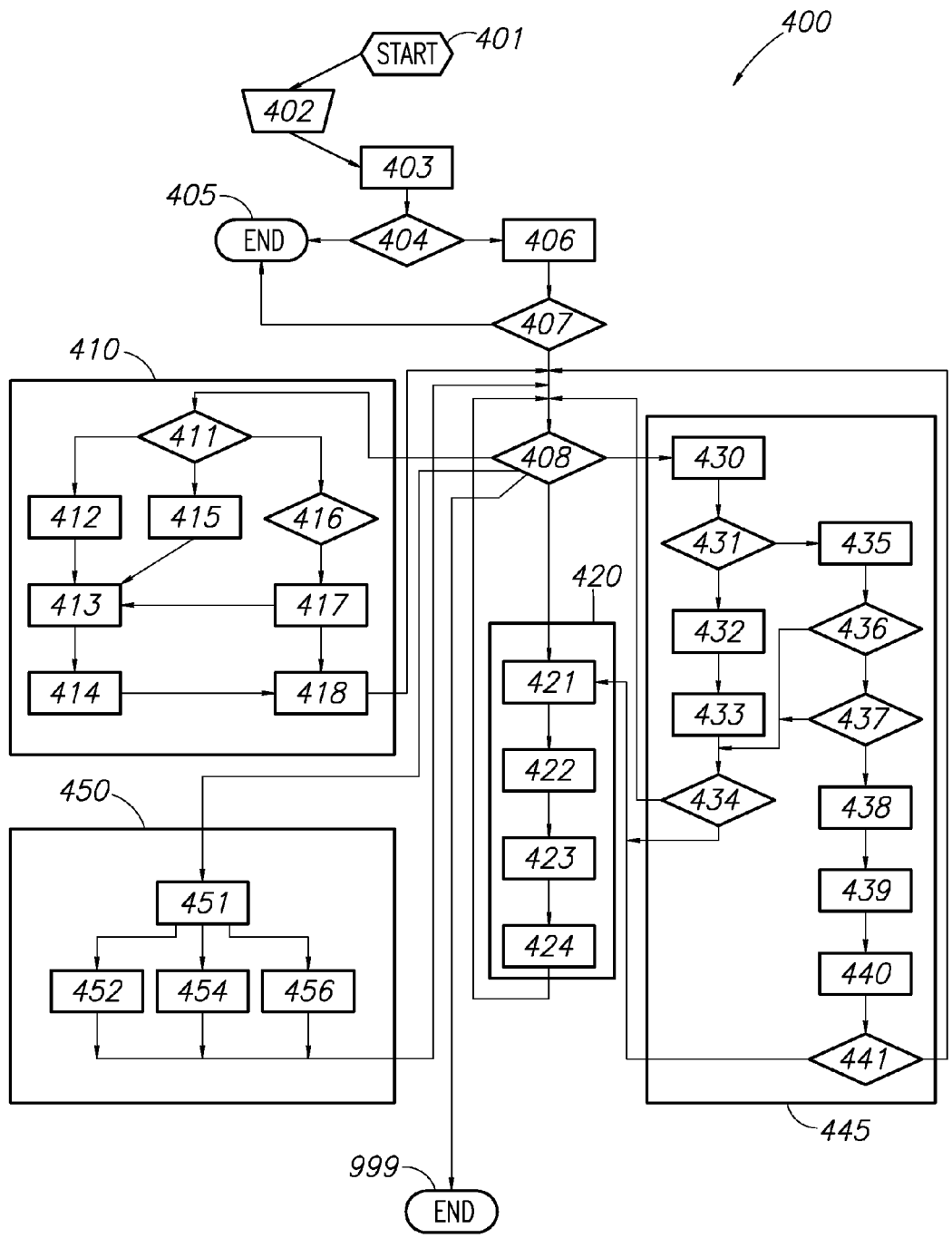
FIG. 4 is a schematic illustration of an embodiment of the present invention related to one possible flowchart of the process for the use of the invention apparatus while interphasing to a cellular phone or a host personal computer for activation of various operations between the cellular phone and the apparatus, while using the cellular phone or the host computer display and keyboard hardware and functions.

One possible flow-chart of the sequence of steps and related process, generally designated 400, needed for the use of the invention apparatus while interphasing to a host personal computer, or to a cellular phone, for activation of various operations between the cellular phone/host computer and the apparatus, while using the cellular phone display and keyboard operational functions, or the host PC monitor and keyboard, for the user's interaction with the invention apparatus, is shown in FIG. 4.

Stage 401 connects the apparatus 100 to the cellular phone mini USB or compatible connector or connecting apparatus 100 regular USB to a personal computer and then the user is switching on the apparatus 100.

Stage 402: checks whether the user is properly holding the apparatus 100 in his palm to enable reliable and accurate sensing of the apparatus integrated set of sensors.

In stage 403, the user is starting executing the apparatus 100 user's authentication sequence through the execution of the holding user biometric required parameters testing process, which is based on the measurement and processing of at least three biometric parameters (as described herein in one preferred embodiment). As will be appreciated by persons knowledgeable in the art, in another embodiment, fewer biometric parameters, such as at least two parameters, may be processed. In executing a biometric testing process: First tested parameter is a life sign indication sensor output either his pulse rate that should be normal in a predefined normal non active state range, say 50-80 PPM, or his $O_2$ saturation level that should be in the normal range of 90-100%, or both should be normal, or his body temperature that should be in a normal range of 36-41 degrees centigrade. Second tested parameter is to measure and evaluate the first one of the user's two biometric measured parameters, such as one or two of his fingers fingerprints, and/or the apparatus holding user face pattern set of measured parameters and/or the user measured and analyzed iris pattern. Third tested parameter is to measure and evaluated the user second measured biometric parameter, such as one or two of the user fingerprints, and/or the apparatus holding user face pattern set of measured personal parameters, and/or the user's detected eye iris pattern.

In Stage 404, the at least three presently measured parameters are authenticated when compared and analyzed by the apparatus 100 internal controller and data processing unit 160. The at least three presently measured parameters are compared to the previously measured, analyzed and stored identical at least three parameters of the same apparatus owner stored in memory unit 140, Upon authentication a positive response is created by the apparatus 100 and it continues to stage 406.

If the authentication process fails, then the apparatus 100 controller unit 160 shifts the apparatus 100 to stage 405, wherein the apparatus shuts itself off and blocks the apparatus from further use or operation for a predefined time duration.

In stage 406, the apparatus unit 160 sends to the cellular phone or to the host it is connected to through interphasing unit 110, a request to identify the operating system on which the phone or host unit is running on.

In stage 407, if the unit 160 gets a positive response of identifying a known operating system that is in the apparatus memory bank then it initiates the operation of the related stored operating system dedicated communication interphasing SW package and it continues to stage 408, Otherwise it goes back to stage 405 wherein the apparatus 100 controller unit 160 is shutting-off the apparatus and blocks the apparatus from further use or operation for a predefined time duration.

In stage 408, the apparatus initiates a main menu screen, displayed on the cellular phone or host PC screen enabling the user to select between four options:

A: 410—retrieving stored data from the apparatus's memory going to stage 411;

B: 420—saving a file from the host or the cellular phone memory into the apparatus memory 150 or 190, going to stage 421;

C: 445—searching in the internet for a website of a selected medical institute, or financial institute, or other, going to stage 430; and D: 450—by selecting in the menu to go to stage 451, it is exposing to the user a frame that enables the user to select, retrieve or update data and information from and into the apparatus 100 stored data that creates for the user a handy organizer function, including the user's various types of needed to be easily accessible personal stored data, that includes a personal tabular data-base of all the user's set of his registered member data for his frequently visited websites 452 and official certificate cards 454 and point of sale service providers 456.

Stage 452 provides the user with the user's ID numbers, User names and password codes for all his favorite websites that require registration and personal organizer, as well as the user's personal phone book and important memos Another option which may be selected is 456 in this menu. It is implemented in case of a user using the apparatus for purchasing at a store; the user can show the merchant his apparatus's stored face picture, so the merchant can compare it to the user face that he observes in real time before approving and finalizing a transaction with the user. Option 454 is all the official cards (certificate) a man need like passport, driving license and so on.

The process may be terminated by selecting and shifting to final stage 999.

In stage 411, the user is exposed to a new screen of the cellular or the PC host display with options to select from: A) selecting 412 for medical data; B) selecting 415 for financial data; and C) selecting 416 for other personal data.

In stage 412, the apparatus initiates a menu displayed on the cellular phone or host screen, wherein the user can select from the options:

A) injured/checked body part, B) ID code of the requested medical doctor, C) required HMO (medical insurer) and D) Required hospital, then moving to stage 413.

In stage 413, the apparatus initiates internal memory search for retrieval and display of the relevant data stored in its memory units 150 and 170.

In stage 414, the apparatus supports operating usable applications enabling the user to compare stored medical/financial/other data from various periods/dates and data sources;

In stage 418, the operational sequence take the apparatus back to stage 408 where the user can select a new option In stage 415, the user can select from the related hierarchical composite screens by using typical keywords for feeding in, or retrieving the user personal DB stored data retrieval, from the 5 or more keywords search options: A) Bank B) Insurance company/financial institute, C) Date, D) Credit/Debit transaction deal, E) Type of expenditure/income counter account for the transaction, then the sequence moves back to stage 413 to retrieve from the database.

In stage 416, the user gets a menu screen to select a subject to retrieve stored data from the subjects used as search keywords.

In stage 417, the user select keys to retrieve the data refers to the subject he has chosen in stage 416, than—goes to stage 413.

Stage 421 refers to saving new data logically emerging from stage 408 main menu, a screen appears on the display of the host or the cellular phone, requesting keywords for data storage—file subject and date are the main keywords and the user can select up to 5 additional data storage keys, suggested from a readymade list, said list is different for each subject like described in stages 411 and 415.

In stage 422, the apparatus controller adds one digit to the last processed user's personal data base record number and this number will be the record number to the newly saved record in the apparatus memory.

In stage 423, the controller creates an encrypting code for each newly processed Record and saves it into the apparatus 100 secured mass storage module 170.

In stage 424, the apparatus 100 controller 160 shifts the user screen back to stage 408 menu selection screen.

In stage 445, the user selects the menu option of getting access to the Internet.

In stage 430, the user sees on the host or cellular phone screen a list of preferred favorite sites which have in the personal secured data of the apparatus's personal user. In stage 431, if the user clicks on any one of them then the controller moves to stage 432, or if the user clicks in an open data feeding field new website address, then the controller 160 moves the sequence to stage 435.

In stage 432, the controller 160 detects the URL (internet address) of a user selected preferred favorite website and then the controller feeds in from the memory 150 the stored specific site predefined user name and password into the selected page user ID data feed spaces to enable the user to get easy and automatic access to any such selected favorite website as a registered and access authorized member.

In stage 433, the host or the cell phone automatically moves to display the first registered user's website entrance screen at the selected website address, to display the selected site registered members home page and to enable the user to further interact with the selected website and associated personal data he may wish to find there, like his personal medical tests results, prescriptions and bank statements.

In stage 434, a screen appears requesting the user to either save his personal data he got from the website he has visited going back to stage 421 how to save this day and under what search keys, alternatively the user can go back to stage 408 where he can choose another apparatus operation optional activity from the main menu.

In stage 435, the user gets an internet screen and he types a new address as he likes and gets his wanted information. In stage 436 the controller generates a two options selection screen one is to save the retrieved personal results in the Device 100 memory then it goes to stage 434, otherwise it suggests the user to purchase a service or a product than it goes to stage 437.

In stage 437, the user is asked if he wants to use the details of the credit card from the apparatus Stage 438 requests the user to define the kind of credit card the user wants to execute, and the selected purchase transaction, after selecting the preferred user credit card for this transaction, the controller takes from the apparatus's secured memory 170 the file containing the user's credit card number, the user name, card expiration date and the other card secret code number and sends this data to the vendor (stage 439).

In stage 440, the transaction is then approved.

In stage 441, a screen appears questioning the user if to save the transaction details and then go to 421 and if not the user may be transferred and select another activity option from the main menu screen 408.

Stage 999 takes the user out of the apparatus to host operational process and disconnects all communication between the apparatus 100 and the host computer or the cellular phone.

Figure 5:
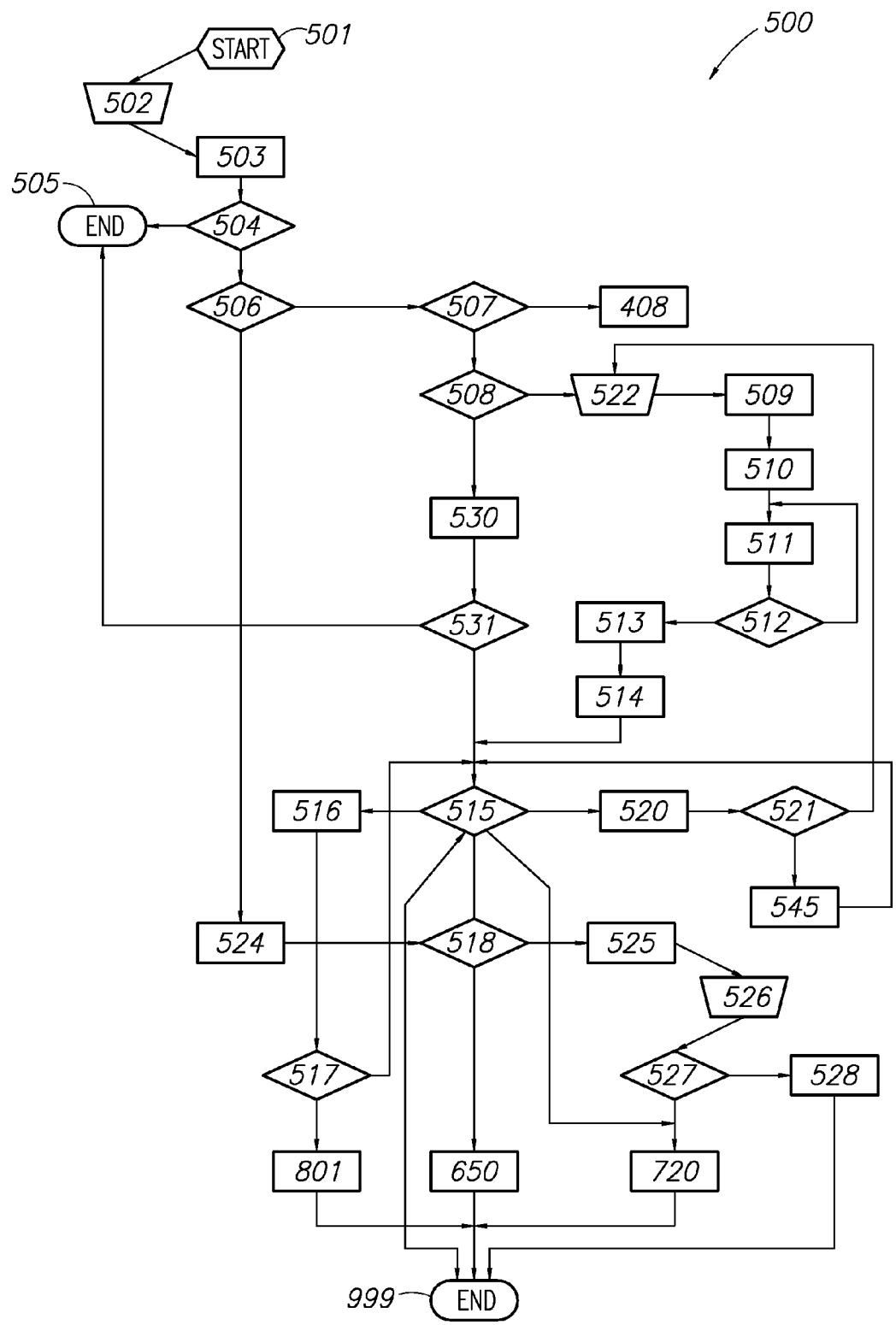
FIG. 5 is a schematic illustration of an embodiment of the present invention related to a possible flowchart of the use of the invention apparatus to interact with the invention system servers, starting from the user's authentication and up to the stage of the user getting an approved access to the systems servers' data and for his further interactions with the system.

A possible flowchart of the process steps, generally designated 500, associated with the use of the invention apparatus while a user is establishing a connection with the invention system and applying the invention apparatus to be authenticated and get access to the system servers, is shown in FIG. 5. The described process 500 in this flowchart is starting from the user authentication stage up to the stage of getting an approved access to the system servers' data and for the user further interaction with the system to fulfill specific data search and updating tasks, is shown in FIG. 5.

Stage 501, connects the user's apparatus 100 to his cellular phone mini USB or a compatible connector, or connecting the apparatus USB connector to a USB slot in a personal computer, or establishing a Bluetooth wireless data connection between the apparatus and the user's cellular phone, when the user switches on the apparatus 100.

In stage 502, the user holds the apparatus 100 in his palm, pressing his fingers to the fingerprint sensors 270 and 280 as seen in FIG. 3A, looking into the apparatus camera aperture 260 and/or focusing his line of site to the center of the iris imaging sensor aperture 265. In parallel, on the other side of the apparatus, the user is attaching his palm to the physiological sensor aperture 250 which senses' the user's heart bit rate and his blood oxygen saturation level sensing his blood then pressing the on/off button 290 that starts the authentication process.

In stage 503, the apparatus then executes a biometric sensing and testing sequence of the holding user three biometric parameters. One is a life sign indication sensor (128) output, either his pulse rate that should be normal in a predefined normal non active state range, say 50-80 PPM, or his $O_2$ saturation level that should be in the normal range of 90-100%, or his body temperature that should be in a normal range of 36-41 degrees centigrade. The other two measured and evaluated parameters are the user's one or two of his fingerprints, and/or grabbing and processing the holding user face pattern set of measured parameters, and/or the user eye iris image grabbing and then analyzing the iris image structure and pattern.

Stage 504, is a junction point for options evaluation and decision stage. If the user's measured and processed set of bio parameters fits to the apparatus's original user's first registration stored set of bio parameters in unit 140, then the process continues to stage 506, otherwise the process stops at stage 505.

In stage 505, the user receives a text message on the connected cellular phone or host computer screen that the authentication process failed and the apparatus then shuts off and the user needs to restart and repeat the same process till that stage.

In stage 506, the apparatus controller checks the results of the user's now measured life indication sensor output and if the measured parameters are different in more that 15% than the user's moving average results of previous life indication tests, then it goes to stage 524 if the difference is less than 15% then it continues to stage 507.

In stage 507, the user gets a menu screen on the host or cellular phone display that enables him to choose either to be connected with the invention system for further interaction in stage 508, or to continue working only on interactions with his host computer or smart phone, in stage 408 as described in process 400 above.

In stage 508, if the user is a new user that it is his first interaction with the invention system, then he has to pass a testing and verification procedure to verify that he is the legitimate owner of the specific apparatus having the apparatus's registered product embedded serial number and therefore the process continues to phase 522 which requires the user to visit in person a service station of the invention system and identity himself in person as well as his personal apparatus in front of an employee of the system, a procedure which will be done in stage 509. If the user is not a first time system entry user, then the process goes to stage 530.

In stage 509, the user identifies himself in front of the system employee by showing his national ID card and at least one additional ID document such as a passport or a driving license, for example, then the invention system employee reads the embedded serial number of the apparatus by connecting the apparatus to the system computer terminal and then this number is automatically fed into the system memory to the same temporary file where the employee will manually feed the user's set of ID data including his national ID number, nationality, full name, date of birth and his residence address.

In stage 510, the invention system registers the user as a new customer and opens a dedicated new customer basic data file in the system memory and allocating for that user data file a predefined dedicated and private memory space in the non secured section of the system memory. The system manager registers each user and stores the personal ID data file of each user in a memory sub-system connected to the system. The registration further includes an additional step wherein the system manager generates for each user N pairs of two different randomly selected alphanumeric characters strings; each of said strings is combined of n alphanumeric characters in length.

The system manager stores the N pairs in the system memory sub-system and also sends the n characters strings N pairs to be stored in the user personal apparatus. In stage 511, the apparatus, while still connected to the system computer terminal, generates a random alphanumeric data string with L characters that will serve as the unique user secret access code to his secured private memory partition in the system memory.

In stage 512, the processed L characters string is fed to the invention system and is checked by the system computer if the processed L characters string has not already been processed and fed to the system memory in the past by another registered user's apparatus. If the system computer finds in its records an identical memory ID data string of another already registered user then it goes back to stage 511 and then the apparatus generates a new randomly selected string of L alphanumeric characters. If the system could not find in its records an identical memory ID data string already dedicated to and serving another registered user, then this string is selected to be the new secret access code for the newly registered user.

In stage 513, the system computer creates for the newly registered user a secured private memory space in the system mass memory that it will be defined and will be further allocated for this user and could be accessed only by using the specific user secret access code with L characters data string, which is stored only in the user's own apparatus.

In stage 514, the user and the system employee receives a written displayed message from the system computer saying that the new user registration has ended successfully and the user can from now on work with and interact with the invention system from any remote location while using his registered personal apparatus for identification and authentication. The user and his apparatus when connected to any cell phone or host computer can now be transferred to work in stage 515.

In stage 530, and upon normal initiation of communication between the system manager and each user, the system manager may further communicate with the user and first compare the user's ID data file and his personal apparatus unique embedded characterizing serial number, as stored in the user's personal apparatus, with the corresponding user's and apparatus's identification data stored in the system memory module. If the two sets of identification data match, then the system manager sends a first string of the stored N strings of coded alphanumeric data to the user's apparatus and the user's apparatus responds with the second matching string from the same stored pair of coded alphanumeric data uniquely associated with the user's apparatus and the system manager compares the received second string of coded alphanumeric data with a second string of coded alphanumeric data pre-stored in the system's memory. Then the system manager compares for consecutive M out of N times the received additional different strings of coded alphanumeric data pre-stored in the memory of the user's apparatus that is associated with the unique user, with the additional strings of coded alphanumeric data pre-stored in the memory of the system.

In stage 531, if all M strings of coded alphanumeric data match, then the system manager authenticates the user and permits the user access to the system and the process goes to stage 515. Otherwise, the system goes to stage 505 which ends the session.

In stage 515, the user is already a system registered user and can be connected to the system after a short identification and authentication sequence, as detailed herein. In this stage, the user selects from the main menu displayed to him on his host screen; he can choose the option to work and interact with the system and can choose between several interaction options. If the user chooses to work in the unsecured part of the system-stored data, the user chooses the menu option that transfers him to stage 520. If the user chooses to work in the user's secured and protected part of the system stored data, then he chooses the menu option that transfers him to stage 516. If the user chooses to work and interact through the systems on his financial and insurance issues, the user can do it through the system and can get safe and secured access to all his relevant banking services, insurance companies, investment houses, pension funds, etc. All the relevant data is being easily accessed and managed by the system through a dedicated menu screen, the user chooses the menu option that takes him to stage 518. If the user chooses to work and interact through the systems on his medical issues and through the system to get access to all his relevant medical services, hospitals, and clinics data, all managed by the system through a dedicated menu, the user chooses the menu option that takes him to stage 720. If he wants to end the interaction with the system, the user chooses option 999 that closes the communication with the system, In stage 516, the user's apparatus sends, via the host or cellular phone that is connected to, the system, secured access code which is the memory ID data string created in stage 512.

In stage 517, if the string is recognized as a legitimate string associated with the user, the processes continues to 801, otherwise it shifts the user to stage 515 and shows him again the main menu with several choice options.

In stage 518, the system checks at the background all the time if the user has pressed on the emergency button, or alternatively in stage 524 if the physiologic sensor detects abnormality in the user physical condition and it sends an alarm that the user is not in a normal health condition. If an emergency is indicated, then the system goes to stage 525, otherwise it continues to stage 650 for processing financial oriented activities. The system continuously checks that the user is connected to the financial section of its services, if the user has pressed the emergency button of his apparatus, or alternatively in stage 524 if the physiologic sensor detects abnormality in the user physical condition and it sends an alarm that the user is not in a normal health condition, and if yes the system goes to stage 525 and the user's interaction with the system supported financial services section, stops.

In stage 520, the user (after the stage of requesting interaction with non secured data and the user's apparatus) is requested by the system to transfer to the system the ID data of the user and the apparatus embedded serial number from the apparatus memory.

In stage 521, the system checks if the numbers and data stored in its memory are matching those received from the linked user's apparatus and if positive it continues to stage 545 for further interaction with the system and external services providers and if not it goes to stage 522 for a second authentication stage.

In stage 522, a second human operator based authentication sequence is undertaken with the user at the system clients security center, to check if the apparatus belongs to the user that holds it, this process is carried out every time the system does not authenticate the user during any of the user's access checking stages, as detailed in stages 516 and 517 and/or in 520 and 521. The employee at the system security center checks if the legitimate apparatus user face picture stored in the apparatus memory matches the face of the user that came to the office; the system employee also asks the user to operate an authorization process with the apparatus he claims is his, in front of the system employee. If that second human supervised authentication process results are negative then it starts a security investigation with that user.

Stage 525 is related to an emergency case message received at the system's special control and emergency management center 348. The center 348 team automatically receives, from the user's apparatus through the communication lines, the entire user's ID data stored in the user's apparatus including his national ID number and his medical insurance number and the name of the medical insurance company is registered in. In addition, the center 348 team receives the data on the user's emergency contact person as stored in his apparatus memory In stage 526, the emergency center team may contact this person via his cell phone and also contact and request the user's emergency case contact persons to get to this person detected location, as soon as possible.

In stage 527, if the emergency center is calling and the user is answering his phone and requesting for medical or other type of immediate help, then the process goes to stage 528. Otherwise, the user may get access to his most updated medical records stored in the system memory, in a process undertaken in stage 720 and then the user may download them to his apparatus through the host computer or cell phone, before he goes by himself to get medical assistance.

In stage 528, the emergency center team are calling the user location rescue team nearest to the user and giving them by phone the user's exact location and a briefing on the user's medical emergency case records, as stored in his personal apparatus. In parallel, the emergency center team updates all the medical records of this user, stored in the system memory and prepares a full medical file report on this user, which is transferred electronically or by fax to the emergency room team in the selected hospital—to which the rescue team are intending to take the user to, for further treatment.

In Stage 545, the user is connected to a menu that supports all the user's needs to deal with and interact with non-secured personal data and connection related with the user interaction needs with government and municipalities institutes, universities, customers' clubs, for example.

In Stage 650, the user is connected to a menu that supports all the user's needs to deal with and interact with secured personal data related with the user interaction needs with banks, other financial institutes, insurance companies, etc.

In Stage 720, the user is connected to a menu that supports all the user's needs to deal with and interact with secured personal data related with the user's interaction needs with hospitals, In stage 801, the user receives on his host display the menu related to storage and retrieval of his secured personal data to and from his personal apparatus.

In stage 999, the user interaction with the system ends, or the user may choose to be transferred back to the interaction with the system main menu, which is represented by stage 515.

Figure 6:
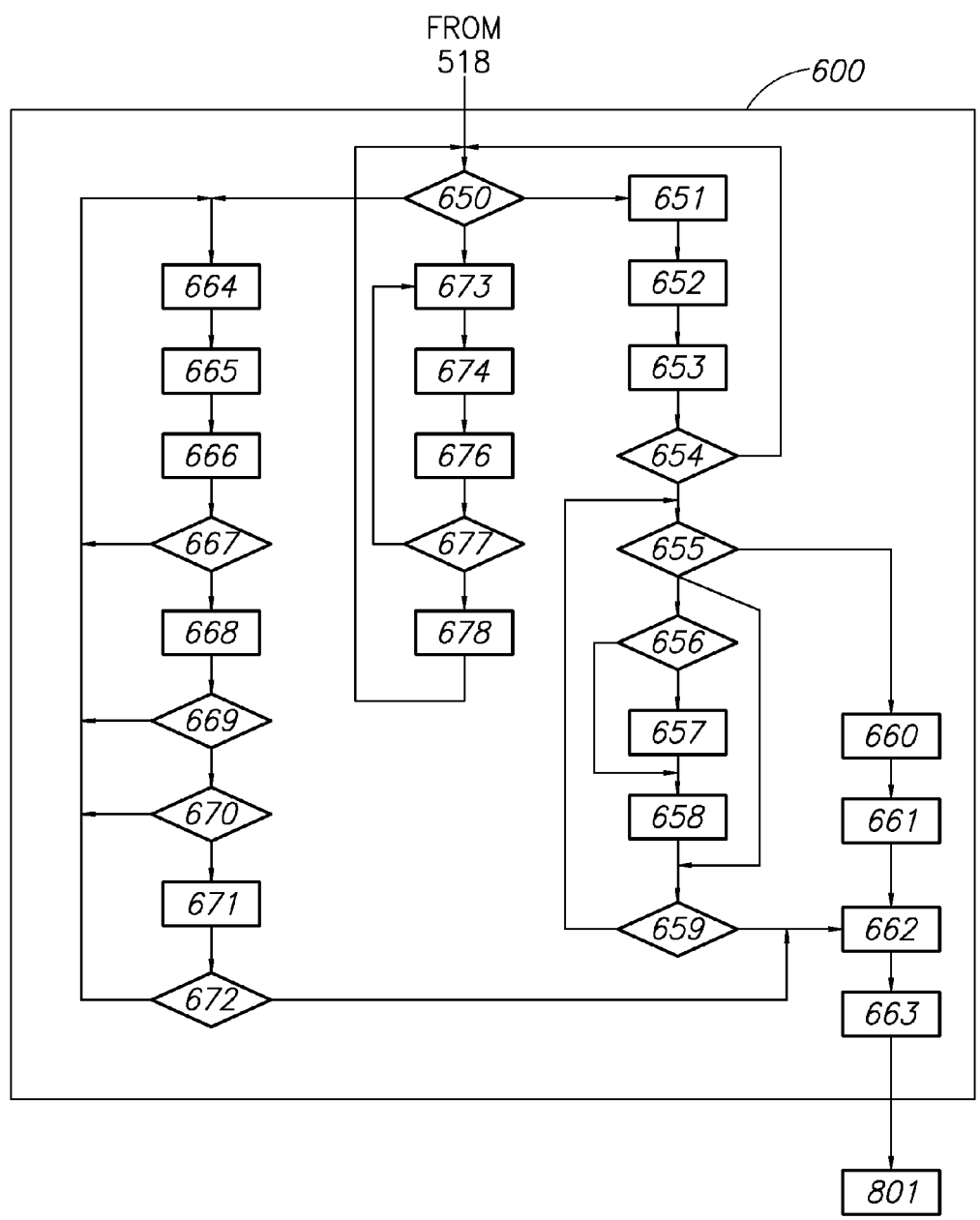
FIG. 6 is a schematic illustration of an embodiment of the present invention related to a possible flowchart of the mode of usage of the invention system, wherein a user applying the invention apparatus to interact with the system servers, starting from the stage of the user getting an approved access to the systems servers' data and then the user's further interaction with the invention system to execute various types of secured financial transactions.

Another possible flowchart of the process steps, generally designated 600, associated with the use of the invention apparatus and the user interaction with the invention system done after the stage wherein the user is positively authenticated and obtains an approved access to the invention system and then establishes a connection with the invention system. The described process 600 in this flowchart is starting from the stage when the user is obtains a secured access through the system to various kinds of banks, credit card companies and financial institutes, as needed to fulfill specific related data searches and for records updating and executing financial transactions the process starts when the user has reached the first stage and start of process 600 in the invention system user's access creation process, is described in FIG. 6.

In the first stage 650 of process 600, the user receives a menu screen enabling him to choose a credit card company shifting to stage 664, a bank company shifting to stage 651, or to an insurance company shifting to stage 671. If the user dose not wants to proceed in any of these routes, he can choose to go back to the previously described stage 515 in FIG. 5.

In stage 651, the user has chosen the bank selection option and obtains a list of the system registered banks menu, to select the bank he is interested in, or that he has an account in it.

In stage 652, the invention system is connecting through a highly secured communication line with the user's selected bank and the specific branch he works with.

In stage 653, the user's apparatus is sending to the selected bank and branch the user's bank account and the user's ID data (e.g. username and password) in the format requested by the specific chosen bank.

In stage 654, the bank computer is allocating in its memory the specific user registered bank access permit data details and the account status and compares them with the user's related details derived from the user's apparatus memory, if the details are matching and the requested bank account is found in the bank records, then the process goes to stage 655; if not the user goes back to stage 650.

In stage 655, the user receives a menu to choose from, retrieving details from his account or executing financial transactions. If the user wants to execute financial transactions in his account it goes to stage 656. If the user wants to retrieve the details of a past transaction he will choose and be transferred to stage 660.

In stage 656, the user chooses between charging his electronic purse section in his apparatus secured memory submodule with money, by continuing to stage 658, or choosing a money transfer operation to a third party account by going to stage 657.

In stage 657, the screen of the host, through which the user is securely interacting with the bank's computer through the invention system, requests the user to fill in the empty fields on the screen the name of the third party, his account number and his bank and branch details.

In stage 658, the host screen requests the user to enter into the empty field in the screen the amount to be transferred.

In stage 659, if the transaction is approved by the bank, it goes to stage 662; if not the process goes back to stage 655.

In stage 660, a screen on the host display requests the user to enter the parameters of the financial details he wants to retrieve, regarding the time range of transaction dates or transaction numbers.

In stage 661, the bank retrieves the requested financial data, sends it in a highly secured way via a dedicated communication channel to the invention system, and through the system the relevant user's financial data is then transferred and displayed on the user's host computer screen.

In stage 662, the user receives a screen on his host asking him to choose how he wants to store the requested financial data. He can choose between storing it in his apparatus memory, or in his personal data memory sector at the system data bank, or in both memories in parallel.

Figure 8:
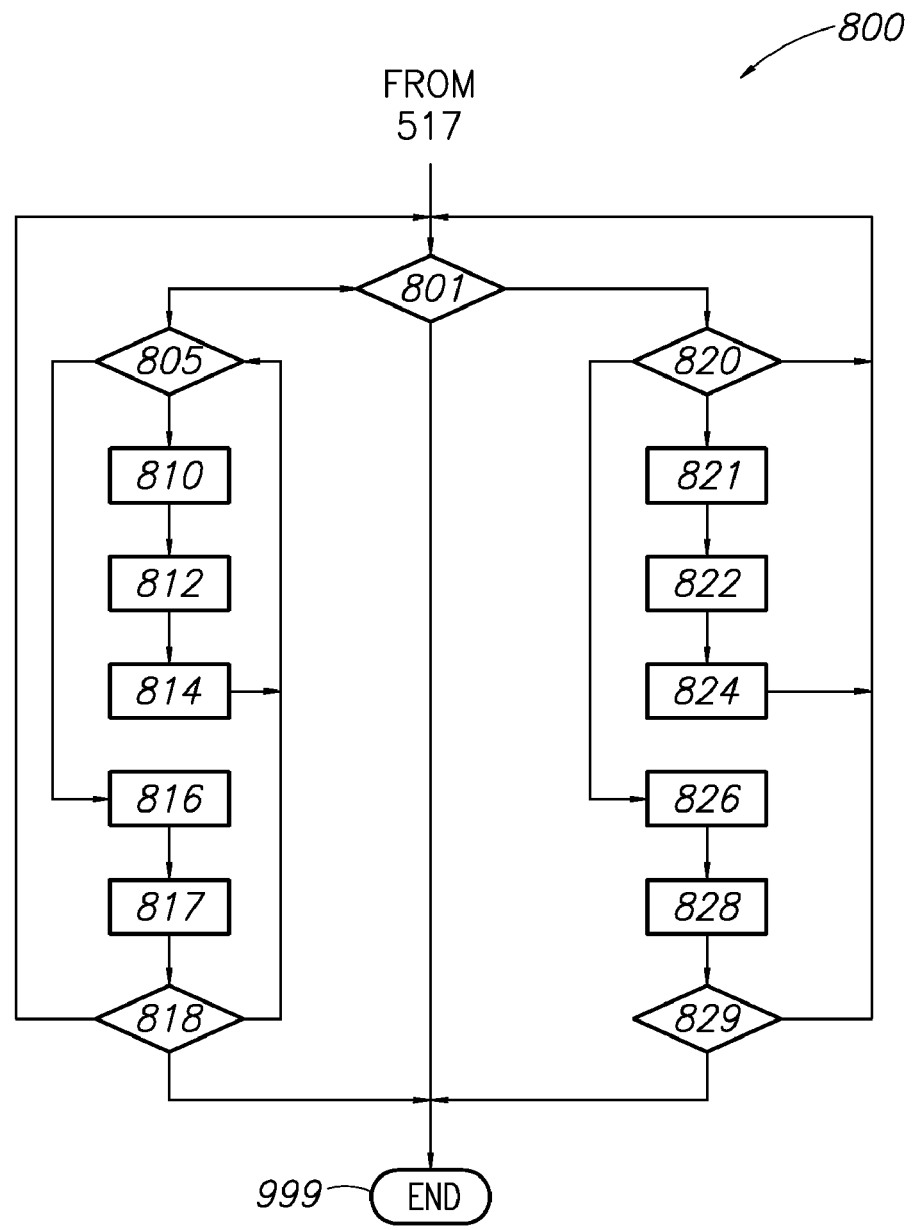
FIG. 8 is a schematic illustration of an embodiment of the present invention related to another possible flowchart of the use of the invention system, for a user applying the invention apparatus to interact with the system servers, starting from the stage of getting an approved access to the invention system servers data and then for further interaction by the user with the invention system as required to execute uploading or downloading of any user' personal data files.

In stage 663, the process goes back to stage 801 as described in FIG. 8.

In stage 664, the user receives a menu screen to choose from a list of credit card companies or to go back to stage 650.

In stage 665, the invention system connects to the selected credit card company.

In stage 666, the user's apparatus sends the credit card company via the system in a secured format, as agreed with the specific credit card company, the user's credit card number and the additional credit card data associated with the user name.

In stage 667, the credit card company may approve the card and the process continues to 668, otherwise the process returns to stage 664.

In stage 668, a screen on the host display requests the user to fill in the details of the entity that should get the funds and the amount of money to credit the selected entity.

In stage 669, the user enters the details of the entity to be credited and if he knows only part of the required details then the user is automatically offered a suggestion by his apparatus on the selected entity full set of details, if he did with the selected entity any previous deal in the past. The selected details are then sent through the system to the credit card company. If the transaction is approved, then the process continues to 670, otherwise it goes back to the beginning of the interaction with the credit card company stage 664.

In stage 670, the credit card company approves the transaction and continues to stage 671; otherwise if the transaction is rejected, the process goes back to stage 664.

In stage 671, the credit card company executes the requested transaction and sends, via the invention system to the user's apparatus, a deal approval detailed note.

In stage 672, the user gets a screen asking him if he wants to process another transaction through any credit card company. If yes, the process returns him to stage 664; if not the process goes back stage 662 to keep the transaction in the selected memory choice.

In stage 673, the user receives a menu screen to choose from a list of insurance companies that are approved by the system supervisor and registered at the system server, or alternatively to go back to stage 650.

In stage 674, the system server is contacting and creating direct access to the user's selected insurance company server.

In stage 676, the user's apparatus sends, via the system to the insurance company server, the user ID data plus his registered user name and password at the specific selected insurance company.

In stage 677, the insurance company server approves the user as a registered client and opens for the user direct access to his accounts in the insurance company. If the user's sent ID and access data was not approved, then the user is sent back to stage 673 for another insurance company access trial.

In stage 678, the insurance company gets a specific instruction from the user such as, to download a specific insurance policy to his apparatus, or to update data in another policy and then the insurance company server approves the user's request. At the end of the user's interaction process, the user's access to the insurance company server is closed and the user is sent back to stage 673.

Figure 7:
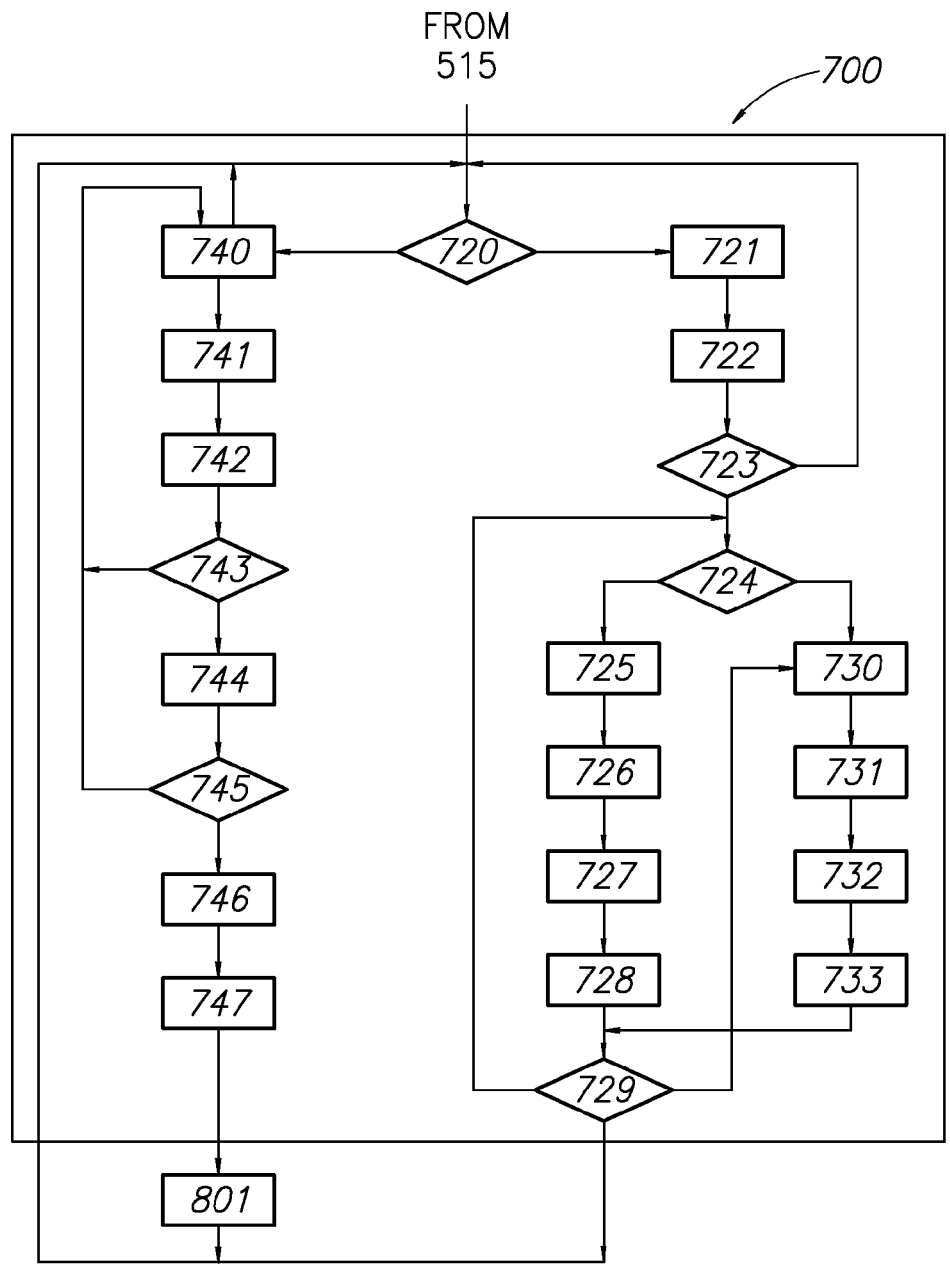
FIG. 7 is a schematic illustration of an embodiment of the present invention related to another possible flowchart of the use of the invention system, wherein a user applying the invention apparatus to interact with the invention system servers, starting from the stage of the user getting an approved access to the systems servers data and the user's further interactions with the system to execute highly secured import and export storage and processing of personal medical files.

Another possible flowchart of the process steps is associated with the use of the invention apparatus and the user interaction with the invention system after the stage of the user is positively authenticated and getting an approved access to the invention system and then establishing a connection with the invention system. The described process in this flowchart starts from the user getting secured access through the system with various kind of hospitals, medical clinics, HMOs and other medial entities and services providers to fulfill specific related data search and for records updating and executing updating of the user's medical records, is shown in previous FIG. 5 where the process starts when the user has reached stage 720 in the invention system user's access creation process 700 described in FIG. 7.

In stage 720, in process 700 the user has received full access to the invention system as described in FIG. 5 and the user has selected the option in his interaction screen to get access to the system memory dealing with his medical records and getting secured access through the system to various system registered medical service providers.

In stage 720, the user receives a menu screen requesting him to choose between medical insurance companies (HMO) and then he goes to stage 721, or alternatively to choose hospitals then he goes to stage 740, or ending the process by going back to stage 515.

In stage 721, the system creates secured access to the medical insurance company server that the user is a member of, according to the relevant data in the medical records stored in the user apparatus memory.

In stage 722, the apparatus sends to the medical insurance server the user's member username and medical insurance member ID number and if requested also the user's access password to the medical insurance website.

In stage 723, the medical insurance company server checks if the user medical file ID data fits to the ID and user data that was received from the user's apparatus through the invention system and continues to stage 724 if positive and returns back to stage 720 if negative.

In stage 724, the system requests the user to select between several options in a menu screen he gets on through his host or cell phone display. In option 725, the user may choose making a doctor/clinic appointment. In choosing option 730, the user requests all his past medical tests results, otherwise the user is directed back to stage 720 and then stops if no further action item is selected by him.

In stage 725, the user receives a screen from the medical insurance through the system and to his host display requesting the user to select the type and the name of the medical doctor he wants to meet.

In stage 726, the user gets a screen with the reception open dates, hours for the selected doctor.

In stage 727, the user is selecting his best date and time choice for appointment to the selected doctor.

In stage 728, the user receives from the medical insurance computer a final confirmation notice on his host screen regarding the user's final approved medical appointment time and day, then goes to stage 729.

In stage 729, the user receives a menu on his host screen display to choose if he wants to make another appointment. Then he may move to 725 or to see his past medical tests results he goes to 730, or to return to main menu 720 or to save in stage 801.

In stage 730, the user receives on his host screen display a menu screen from the medical insurance server, to select the medical tests results he wants to review.

In stage 731, the user selects the requested tests results and the user's apparatus forwards to the host screen the most updated results the user has in his apparatus memory on this specific test, if any.

In stage 732, the medical insurance company server searches its memory records to check if it finds more relevant updated tests data on this user and then it sends the found files to the user's host to enable the user to select either to display the results on the screen or/and to save them in his apparatus memory for long term storage.

In stage 733, the user selects his choice on the processing of the retrieved medical tests results and the system goes back to stage 729, which may connect to the save stage 801 in FIG. 8.

In stage 740, the user receives a menu screen on his host display to choose a hospital from a list, or to return to stage 720. He then chooses the preferred hospital from the list and then goes to stage 741.

In stage 741, the system server contacts the selected hospital via a secured communication channel it has with each of the hospitals in the displayed list and creates an open communication link with the hospital server.

In Stage 742, the user's personal apparatus sends the user's ID data file including full name, ID card number and details.

In stage 743, the selected hospital server checks if it has in its records that the specific user was a hospitalized patient or was treated by the hospital's clinics; if yes goes to stage 744, if not, it goes back to stage 740.

In stage 744, the user receives a screen with a menu requesting him to choose if he needs a hospital release medical report, or medical tests results and the user selects his choice.

In stage 745, the hospital server searches for the selected data files and goes to 746 if the requested data files were found, and if not, the process goes back to stage 740.

In stage 746, the user receives the information from the hospital on his host screen.

In stage 747, the user receives a menu screen requesting him to choose where to store the retrieved hospital data in the system memory wherein the user's personal medical data files are stored, or in the user's personal apparatus memory, or in both then it goes to stage 801.

After the new medical files are saved and stored in one or two of the selected storage memories in stage 801, then the process goes back to stage 720, where the user gets a new menu screen to start another medical data processing sequence with the invention system and with external medical services providers or goes back to stage 515 in FIG. 5.

Another possible flowchart of the a dedicated process steps, is associated with the use of the invention apparatus and the user's interaction with the invention system, after the stage in which the user is positively authenticated and getting an approved access to the invention system and establishing an open connection link with the invention system. The described dedicated process in this flowchart is related to the steps of the user needs to store and retrieve data in and out of the system memory bank, the related processes are described in FIG. 8 which covers the process 800 of data storage and retrieval in the invention system memory.

In step 801, the user is requested by a menu on his host screen to choose between retrieval of data from the system memory and then the process goes to stage 805. Alternatively, if the user selects the option to save data in the system memory, then the process goes to stage 820, or if the user wants to end this process it goes to stage 999.

In step 805, if the data requested is from the non-secured data memory partition of the system mass memory bank, then the process goes to 810, or if the user needs to retrieve secured data from the secured data partition of the system memory the process goes to 816.

In stage 810, the user's personal apparatus send the user's ID data file.

In stage 812, the system server approves the user's ID and requests to get from the user his selected data retrieval keywords, to enable the system server to find the requested data from the system's memory vast data base.

In stage 814, the system server approves the selected search keywords, finds the requested data files according to the given keywords and returns to stage 805.

In stage 816, where the user has selected in stage 805 the option to retrieve secured data files, then the user's apparatus sends to the system server for secured identification, the apparatus' memory stored L alphanumeric characters of the secured access code, security string, that was generated in the first user's registration stage activities at the system server and is stored both at the apparatus memory as well as in the system memory sector that stores the specific user data.

In stage 817, the system server requests the user to enter the requested secured data files relevant DB access keywords and goes to stage 818.

In stage 818, the system server retrieves the user requested secured data files according to the user's selected search keywords, then the user is requested through the host if to return back to 801. If the user wishes to store further data or initiate the retrieval sequence, he returns to 805, or he may go to end stage 999 and stop.

In stage 820, the user is requested through a menu screen in his host, to save the retrieved or the new data in the system non-secured data memory sector—stage 821, or if he wishes to store the new data in the system secured data memory sector he goes to stage 826, or to go back to stage 801 to restart the entire process 800.

In stage 821, the user's personal apparatus sends the user's ID card number.

In stage 822, the system server requests the user, while connecting to the user through the host or the cellular phone he is connected to, to get the user's selected data base save and retrieval keywords for the specific new data file the user wants to save in his personal files sector in the system's database.

In stage 824, the personal apparatus encrypts the specific file in process and sends it for the user's retrieval to the user's personal files sector in the system's database and then return to stage 801.

In stage 826, the personal apparatus sends to the system server the hidden user-system agreed identification string of L alphanumeric characters of the secured access code.

In stage 828, the system sever requests the user to define and send the user's selected data base save and retrieval keywords for the specific new data file the user wants to save securely encrypted in his non accessible personal files sector in the system's database.

In stage 829, the personal apparatus encrypts the user's file and then sends it to the system server to be stored in the system's secured and encrypted data files memory sector. Then the user can select if to repeat the data handling process and go to stage 801 or to end the process and go to end stage 999.

In stage 999, the process ends and the user is disconnected from the system server and from his personal apparatus which also shuts down.

Referring now to FIG. 9, which illustrates the dedicated device 1000 related to the present invention, serving as one possible embodiment of a charging and user personal data backup device for the invention apparatus. FIG. 9 demonstrates a conceptual modular structure and the related device internal sub-modules layout and functionality for the present invention apparatus's charging and data backup device.

Block 1010 in FIG. 9 is the device 1000 mains plug-in charging module that includes the device 1000 charging plug 1012 for its connection to the mains supply, an AC-DC converter unit 1014 and a power supply unit 1016. Unit 1014 converts the mains AC voltage to DC voltage and the power supply 1016 generates from the converted DC voltage, all the DC voltages that are required to drive the device 1000 electronic sub-module 1020 various electronic components.

Sub-module 1040 includes a battery charger and a rechargeable battery, to enable power backup and safe operation of the device 100, in case of lack of voltage supply from the mains electrical power. Sub-module 1020 is the device main electronic module that includes a micro processor and associated electronics sub-module 1024 and a mass memory, solid state, flash memory based sub-module 1028, that is of a similar memory capacity size, when compared to the memory units 150 and 170 combined data storage capacity in the apparatus 100. The electronic unit 1020 automatically checks the memory sub-module 1028 updating requirements, whenever the apparatus 100 is connected through its interphasing data plug 110 to the device 1000 connection plug unit 1030. Processor sub-module 1024 checks the apparatus 100 last updating date and its related secured and non secured memory data content and status and if it is more updated then the data stored in the memory 1028 of the device, then it creates a mirror image of the apparatus 100 memory sub-modules 150 and 170 content, in memory unit 1028. In case that for some reason the memory content of the apparatus 100 is erased or injured, then the sub-module 1024 detects it and automatically updates the apparatus 100 memory units 150 and 170 with the last version of the data stored in memory module 1028 of devise 1000.

Sub-module 1050 is an electronic buzzer activation module that operates upon pressing a button, located on the device 1000 housing, an RF transmitter also integrated in this sub module 1050. When a user needs to allocate the exact position of his apparatus in the home or office environment, the user presses the module 1050 buzzer button, then the integrated RF transmitter sub-module 1050 transmits a coded signal to the Buzzer RF receiver sub-module 198 embedded within the apparatus 100 housing and then the detected coded signal activates an electronic sound buzzer that emits an easily detectable sound. The sound buzzer is integrated in the apparatus 100 sub-module 166 and enables the user to easily allocate through the generated sound the position of the apparatus 100 in a room or an open space.

What is claimed is:

1. Apparatus for storing and managing personal and secured data and documentation files associated with a specific user, comprising:
    a plurality of biometric sensors for reading a plurality of personal biological biometric identification parameters of the user holding the apparatus, said plurality of biometric sensors being integrated within the apparatus;
    at least one life signs detector integrated within the apparatus, said life signs detector being configured to measure and record at least one of said user's life sign parameters;
    a first storage unit for the storage of said user's data and documentation files;
    an authentication unit comprising a second storage unit, with said second storage unit configured to store a pre-recorded set of personal biological biometric identification parameters uniquely associated with the specific user, wherein said authentication unit is configured to compare the plurality of personal biological biometric identification parameters of the user holding the apparatus with the pre-recorded set of personal biological biometric identification parameters stored in said second storage unit;
    a processor in communication with said plurality of biometric sensors, said first storage unit and said authentication unit;
    wherein access to the personal data and documentation files stored in said first storage unit is only enabled after said authentication unit positively matches each of the plurality of personal biological biometric identification parameters of the user holding the apparatus with the pre-recorded set of personal biological identification parameters stored in said second storage unit; and
    wherein, whenever any of said at least one life signs detector detects a critical level of said user measured life sign parameters, the apparatus is configured to prevent access to said user's personal data and documentation files stored in said first storage unit.

2. The apparatus according to claim 1, wherein said plurality of biometric sensors are configured to continuously read a plurality of personal biological identification parameters associated with said user holding the apparatus and in the event that a change occurs in any of the plurality of personal biological identification parameters, access to the stored personal data files is denied and the operation of the apparatus is completely shut down.

3. The apparatus according to claim 1, wherein said at least one of said user's life sign parameters is measured by any of a group of life sign indicators including a body pulse rate measurement indicator, a body $O_2$ saturation level indicator, a body heat measurement indicator, an electro-dermal activity indicator, a body respiration indicator and a physical or emotional stress indicator.

4. The apparatus according to claim 1, further comprising:
    communication and data connection means for communicating with an external device, said communication and data connection means being controlled by and in communication with said processor.

5. The apparatus according to claim 4, wherein, whenever any of the group of life sign indicators detects a critical level, the apparatus is configured to initiate an emergency call to any of a group of registered emergency centers, and send to said registered emergency centers any of a group of data files containing information associated with the user, including the identification data file of the user, personal medical data file of the user, the measured set of life sign parameters of the user and location of the user.

6. The apparatus according to claim 4, wherein said apparatus is configured to communicate with any of a group of service providers, said group of service providers including banks, credit card companies, clinics, hospitals and medical insurance companies, municipal and utility entities and websites frequently accessed by said user; thereby allowing said user to access and manage personal data and documentation files, associated with said user.

7. The apparatus according to claim 4, wherein said external device comprises any one of a group including a remote server, a local server, a host computer, voice or data communication means and a cellular phone.

8. The apparatus according to claim 4, wherein said emergency call is initiated via any one of a group of communication means including a secured server, directly via the internet by said apparatus connection and communication means, via the internet through any host computer, via a voice and data communication device and via any cellular phone network.

9. The apparatus according to claim 4, wherein said emergency call is initiated via any one of a group of communication means including a secured server, directly via the internet by said apparatus connection and communication means, via the internet through any host computer, via a voice and data communication device and the cellular phone network.

10. The apparatus according to claim 4, wherein said communication and data connection means comprises at least one of a group of connection and communication devices including a data interface connector attached to a host computer, a Mini USB, a compatible industrial data interface connector attached to a cellular phone, a near field wireless communication interface, a Bluetooth communication interface, a magnetic reader interface, and a smart card reader based on a contact-less communication interface using induction or RF communication.

11. The apparatus according to claim 4, further comprising an integrated software module that automatically detects the operating system of the computer or cellular phone connected to said apparatus through one of said group of communicating devices through which the apparatus is connected, said computer or cellular phone having keyboard and display units associated therewith, thereby allowing the user to interact with said first storage unit and with said processor of said apparatus via said keyboard and display units, whereby said computer or cellular phone is configured to utilize and interact with said memory module, said processor and said sensor module of said apparatus.

12. The apparatus according to claim 1, wherein said first storage unit comprises a detachable and upgradeable miniature PCB board having Flash and/or Nano type solid state read and write memory components with a memory capacity of at least 10 Gigabytes of accessible memory size.

13. The apparatus according to claim 1, further comprising:
- a magnetic strip element that is only activatable after positive authentication of said user's personal biological biometric identification parameters and positive normal non critical measured output of all of the at least one of said life sign detectors of said user measured life sign parameters; and
- wherein said magnetic strip is configured to be concealed within the apparatus and on activation configured to extend out of the apparatus for swiping and reading by any of group of devices including a credit card reader, ATM and point of sale magnetic strip reading device.

14. The apparatus according to claim 1, wherein the processor is configured to securely update the user's data and documentation files.

15. The apparatus according to claim 1, further comprising an integrated digital data encoder/decoder and a wireless transceiver module in communication with the processor, said integrated digital data encoder/decoder and a wireless transceiver being configured to communicate with any of a group of external devices including RF operated credit card readers, ATM machines, and remotely operated electronic locks gates and doors opener using RFID based techniques.

16. The apparatus according to claim 15, further comprising a supplementary base-station device in communication with said wireless transceiver, said base-station device configured to electrically charge the apparatus and simultaneously automatically execute a backup of the internal secured and non-secured stored data of the apparatus.

17. The apparatus according to claim 1, further comprising a power charging and data backup device in communication with the processor of said apparatus, said device comprising;
  i. a charging plug for connecting to the mains supply, an AC-DC converter, a power supply unit and a rechargeable backup battery;
  ii. a micro processor and a mass memory unit;
  iii. an electronic buzzer activator, a button connected to said buzzer activator and an RF transmitter connected to said electronic buzzer activator, wherein on activating said buzzer button, said RF transmitter is configured to transmit a coded signal to the apparatus to enable the user to determine the location of the apparatus; and
  wherein the first storage unit of said apparatus is in communication with the mass memory unit of said device, thereby to compare and synchronize the version of data stored in the first storage unit of said apparatus with the version of data stored in mass memory unit of said device.

18. The apparatus according to claim 1, further comprising an integrated GPS module in communication with the processor to precisely locate the geographical position of the apparatus.

19. The apparatus according to claim 1, further comprising at least one of a group of units including a cellular modem and a flat display, and a touch screen for communication with the processor.

20. The apparatus according to claim 1, further comprising:
- an encryption unit in communication with said processor for the encryption plus compression and for the decompression plus decryption of said user's data files.

21. The apparatus according to claim 1, further comprising:
- an emergency button in communication with said processor and said communication and data connection means module;
- wherein on said emergency button being activated, communication is initiated between said apparatus and any of a group of registered emergency centers, said emergency call transmitting any of a group of data files containing information associated with the unique user of said apparatus, including the identification data of said user, the personal medical data file of said user, and location of said user.

22. A method for managing personal and secured data and documentation files of a plurality of unique users, each one of said plurality of unique users having a personal identification unit uniquely associated with said one user for storing each user's personal data and documentation files, each of said personal identification units comprising:
- a plurality of biometric sensors integrated within the personal identification unit;
- at least one life signs detector, integrated within the personal identification unit, said life signs detector being configured to measure and record at least one of said user's life sign parameters;
- a processor in communication with said plurality of biometric sensors;
- an authentication unit in communication with the processor;
- an encryption unit in communication with said processor;
- a first storage unit in communication with said processor and said encryption unit; and
- communication and data connection means in communication with said processor;

the method comprising the steps of:
  a. the plurality of biometric sensors reading a plurality of personal biological identification parameters of the user holding the personal identification unit;
  b. at least one life signs detector, integrated within the apparatus, measuring and recording at least one of said user's life sign parameters;
  c. said authentication unit comparing each of the personal biological identification parameters of said user with a pre-recorded set of personal biological identification parameters stored in said authentication unit; and
  d. if said authentication unit positively identifies said user, and if all of said at least one life signs detector, records the user's normal life sign parameters, allowing said user access to said user's personal data and documentation files stored in said first storage unit and allowing said user to communicate with other communication means through said personal identification unit.

23. The method of claim 22 further comprising the steps of:
- said biometric sensors continuously reading a plurality of personal biological biometric identification parameters of said user holding the apparatus; and
- in the event that a change occurs in any of the plurality of personal biological biometric identification parameters or in the normal output reading of said least one of said life signs detectors, denying access to the stored personal data files and completely shutting down the operation of said apparatus.

24. The method of claim 22, wherein at least one of said plurality of life signs detectors includes a body pulse rate measurement indicator, a body O2 saturation level indicator, a body heat measurement indicator, an electro-dermal activity indicator, a body respiration indicator and a physical or emotional stress indicator, the method further comprising the steps of:

initiating an emergency call to any of a group of registered emergency centers, whenever any of the life sign indicators detects a critical level; and wherein said emergency call transmits any of a group of data files information associated with the user, including identification of the user, personal medical data file of the user, the measured set of life sign parameters of the user and location of the user.

25. The method of claim 22, wherein said apparatus further comprises an emergency button in communication with said processor and said communication and data connection means, the method further comprising the steps of:

when said emergency button is activated, communication is initiated between said apparatus and any of a group of registered emergency centers; and said emergency call transmitting any of a group of data files information associated with the user, including identification of the user, the personal medical data file of the user, and location of the user.

26. The method of claim 22, further comprising the step of:

communicating, via any one of a group of communication means, with any of a group of service providers including banks, credit card companies, clinics, hospitals and medical insurance companies, municipal and utility entities and websites frequently accessed by said user thereby allowing said user to access and manage said user's personal data and documentation files stored by said group of service providers.

27. The method of claim 22, wherein said apparatus further comprises a magnetic strip element, the method further comprising the step of:

after positive authentication of said user's personal biological identification parameters, activating said magnetic strip thereby allowing said magnetic strip to be read by any of group of devices including a credit card reader, ATM, and point of sale magnetic strip reading device.

28. The method of claim 22, wherein said apparatus further comprises a power charging and data backup device, said device comprising a charging and power unit, an electronic sub unit and a mass memory solid-state memory unit, the method further comprising the steps of:

comparing the memory content of said apparatus first storage unit to the memory content of said mass memory solid-state memory unit; and if the first storage unit of the apparatus lacks data, updating the first storage unit with the last version of the data stored within the solid-state memory unit; and if said solid-state memory unit of said device lacks data, updating the solid-state memory unit of said device with the last version of the data stored within said apparatus the solid-state memory unit.

29. The method of claim 22, wherein each of said plurality of unique users is in communication with a system manager, said system manager managing a remote centralized data communication storage and management system of said plurality of unique users, the method further comprising the steps of:

a. said system manager registering each unique user and storing the personal ID data file of each unique user in a memory sub-system connected to said centralized system; and b. said registration further includes the step wherein said system manager generates for each system user N pairs of two different randomly selected characters strings, each of said strings is a combination of n alphanumeric characters in length; and c. said system manager storing said N pairs in said system memory sub-system and sending said n characters strings pairs to be stored in said unique user personal identification unit memory module; and d. said personal identification unit generating a secret access code of L alphanumeric characters to be further stored in said system memory within a special partition containing the list of said secret access codes for said plurality of unique users without assigning any identification or link between the associated users to his registered secret access code.

30. The method of claim 29, wherein after registration and upon normal initiation of communication between said system manager and each unique user, said system manager further communicating with said unique user and first comparing said unique user's ID data file and said personal identification unit unique embedded characterizing serial number stored in the unique user's personal identification unit with the corresponding user's ID and personal identification data stored in said memory sub-system; and if the two sets of identification data match;

i. said system manager sending a first string of said stored N strings of coded alphanumeric data, to said user's personal identification unit; and ii. said user personal identification unit responding with the second matching string from the same stored pair of coded alphanumeric data uniquely associated with said user personal identification unit: and iii. said system manager comparing the received second string of coded alphanumeric data with a second string of coded alphanumeric data pre-stored in the memory sub-system; and iv. said system manager comparing for consecutive M out of N times the received additional different strings of coded alphanumeric data pre-stored in the memory of said personal identification unit associated with said unique user with the additional strings of coded alphanumeric data pre-stored in the memory of sub-system; and v. if all M strings of coded alphanumeric data match, then said system manager declares authenticating of said unique user and permitting said unique user access to said system.

31. The method of claim 30, wherein after said user gains access to said system, said user chooses either to work with the unsecured parts of said system memory or to gain access to said user secured personal data stored in said system memory by sending from said personal identification unit said secret access code that permits each such user sole access to his private secured memory partition in said system memory.

32. The method of claim 29, further comprising the steps of:

after the step of authenticating, said system manager connecting the personal identification unit of said unique user with any of a group of emergency centers or service providers registered with said system manager at the request of said user personal identification unit; and in the case of a medical emergency call initiated by said personal identification unit, transferring the user's updated medical data to the emergency center.

33. A system for managing personal and secured data and documentation files of a plurality of unique users, the system comprising:

a. a system manager for managing and updating personal data of said system plurality of unique users and for full-duplex communication with each of said plurality of unique users and a plurality of service providers; and b. a storage system connected to said system manager to store updated personal data of each of said plurality of unique users;

c. a plurality of personal identification units, each of said personal identification units being associated with a unique user, each unique user being registered with said system manager, each of said personal identification units comprising a storage unit configured to store the personal ID data file of each unique user and a plurality of biometric sensors for reading a plurality of personal biometric biological identification parameters of the user holding the apparatus, said plurality of biometric sensors being integrated within the personal identification units and at least one life signs detector, integrated within said personal identification units, said life signs detector being configured to measure and record at least one of said user's life sign parameters;

d. a plurality of computer hosts and cellular phones in communication with said system manager, enabling the direct connection by said system manager with said plurality of unique users through their corresponding personal identification unit; and e. a plurality of registered emergency centers and a plurality of registered service providers in communication with said system manager, said plurality of service providers including banks, credit card companies, insurance companies, clinics, hospitals and medical insurance companies, government, municipal and utility entities and selected websites frequently accessed by said plurality of users;

wherein said system manager's access to and communication with the personal data and documentation files stored in said personal identification units associated with each said unique user and to the personal data and documentation files stored by said group of service providers is only enabled after positive authentication of each of said unique user's personal biometric biological identification parameters by said authentication unit and measuring the normal measured output of each one of said user's life sign parameters;

wherein at least one of said plurality of biometric sensors is a life signs detector, said life signs detector being configured to measure and record at least one of said user's life sign parameters; and wherein said at least one of said user's life sign parameters is measured by any of a group of life sign indicators including a body pulse rate measurement indicator, a body $O_2$ saturation level indicator, a body heat measurement indicator, an electro-dermal activity indicator, a body respiration indicator and a physical or emotional stress indicator.

34. The system according to claim 33, wherein each of said plurality of personal identification units comprises:

i. a sensor module comprising a plurality of biometric sensors for reading a plurality of personal biological biometric identification parameters of the user holding the of personal identification units, said of personal identification units being uniquely identified with said user;

ii. a processor in communication with said sensor module for processing said personal biological identification parameters and for processing and managing the personal and secured data and documentation files associated with said user;

iii. an authentication unit in communication with the processor configured to receive and authenticate the identity of said user by comparing said user's personal biological identification parameters read, by the sensor module and processed by the processor, with a pre-recorded set of personal biological identification parameters stored in said authentication unit;

iv. an encryption module in communication with said processor for the encryption plus compression and/or decompression plus decryption of said user's data files;

v. a storage unit in communication with said processor and said encryption module for the storage of said user's data and documentation files; and vi. communication and data connection means in communication with said processor for connecting said of personal identification units with said system manager and plurality of service providers.

35. The system according to claim 34, wherein said system manager is configured:

to communicate with said personal identification units to compare the user's ID data file stored in the unique user's personal identification units with the corresponding identification data stored in said storage unit, and if the two sets of identification data match, then said system manager is configured to initiate a further level of security identification prior to full communication and data updating capability being enabled between said system manager and said user personal identification unit; and wherein said further level of security identification comprises said system manager sending a first string of coded alphanumeric data uniquely associated with said user personal identification unit to said user personal identification unit, said personal identification unit responding with a second string of coded alphanumeric data uniquely associated with said user personal identification unit, and said system manager verifying the received second string of coded alphanumeric data with a second string of coded alphanumeric data pre-stored in the memory sub-system; and said system manager comparing for full matching for N consecutive times received additional different strings of coded alphanumeric data pre-stored in the memory of said personal identification unit associated with said unique user with counter generated additional strings of coded alphanumeric data pre-stored in the memory of sub-system.

36. The system according to claim 34, wherein said plurality of biometric sensors continuously read a plurality of personal biological identification parameters associated with the user holding his unique personal identification units and in the event that a change occurs in any of the plurality of personal biological biometric identification parameters, access to the stored personal data files is denied and the operation of said identification units is completely shut down.

37. The system according to claim 34, wherein each personal identification unit further comprises an emergency button in communication with said processor and said communication and data connection means module;

wherein the personal identification unit is configured to initiate an emergency call to any of said plurality of registered emergency centers, whenever said emergency button is activated or whenever any of the group of life sign indicators detects a critical level; and wherein the personal identification unit is configured to transmit any of a group of data files containing information associated with the user, including the identification data of the user, personal medical data file of the user, the measured set of life sign parameters of the user and location of the user.

38. The system of claim 33, wherein said system, further comprises:
a computerized call center configured to receive phone calls or emergency voice and data messages from any of said plurality of registered emergency centers and a plurality of registered service providers and to communicate with any of said plurality of cellular phone and host computers; and
wherein said call center is configured to communicate the user's location coordinates to an emergency rescue team and simultaneously said call center is configured to communicate with any of said plurality of registered emergency centers and service providers to receive said user's updated medical data and to transfer said data to the user's personal identification unit.

* * * * *